(12) United States Patent
Kamatani et al.

(10) Patent No.: US 8,431,711 B2
(45) Date of Patent: Apr. 30, 2013

(54) ORGANIC COMPOUND

(75) Inventors: Jun Kamatani, Tokyo (JP); Naoki Yamada, Inagi (JP); Akihito Saitoh, Yokohama (JP)

(73) Assignee: Canon Kabushiki Kaisha, Tokyo (JP)

( * ) Notice: Subject to any disclaimer, the term of this patent is extended or adjusted under 35 U.S.C. 154(b) by 187 days.

(21) Appl. No.: 13/140,804

(22) PCT Filed: Dec. 16, 2009

(86) PCT No.: PCT/JP2009/071365
§ 371 (c)(1),
(2), (4) Date: Jun. 17, 2011

(87) PCT Pub. No.: WO2010/071223
PCT Pub. Date: Jun. 24, 2010

(65) Prior Publication Data
US 2011/0251394 A1  Oct. 13, 2011

(30) Foreign Application Priority Data

Dec. 19, 2008  (JP) .................................. 2008-324469

(51) Int. Cl.
C07D 401/10 (2006.01)
C07C 211/43 (2006.01)
C07C 43/20 (2006.01)
C07C 25/22 (2006.01)

(52) U.S. Cl.
USPC ............ 546/255; 564/426; 568/659; 570/183

(58) Field of Classification Search .................. 546/255; 564/426; 568/659; 570/183
See application file for complete search history.

(56) References Cited

U.S. PATENT DOCUMENTS 8,102,116 B2 * 1/2012 Kamatani et al. ............. 313/504

FOREIGN PATENT DOCUMENTS

| JP | 1-289907 A | 11/1989 |
| JP | 2-247278 A | 10/1990 |
| JP | 8-113576 A | 5/1996 |
| JP | 11-12205 A | 1/1999 |
| JP | 11-40360 A | 2/1999 |
| JP | 2003-238516 A | 8/2003 |

OTHER PUBLICATIONS

Journal of Organic Chemistry (1952), 17 845-54.
Journal of the American Chemical Society (1952), 74 1075-1076.
Journal of Organic Chemistry (2003), 68, 883-887.

* cited by examiner

*Primary Examiner* — Charanjit Aulakh
(74) *Attorney, Agent, or Firm* — Canon U.S.A., Inc., IP Division

(57) ABSTRACT

An organic compound is represented by general formula (1):

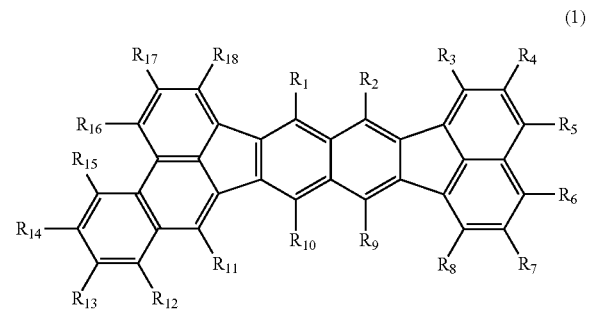

where $R_1$ to $R_{18}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

1 Claim, 3 Drawing Sheets

DIRECTION OF MOMENT

ORGANIC COMPOUND

TECHNICAL FIELD

The present invention relates to a novel organic compound having good emission characteristics.

BACKGROUND ART

An organic light-emitting device includes an anode, a cathode, and a thin film that contains a fluorescent organic compound and is interposed between the anode and the cathode. When electrons and holes are injected from the respective electrodes, excitons of the fluorescent compound are generated and the light emitted by the excitons returning to their ground state is utilized by the device.

Organic light-emitting devices are also called organic electroluminescence devices or organic EL devices.

Recent advancement of organic light-emitting devices has been remarkable and suggested possibilities of applying the devices to a wider range of usages. This is because they can achieve high luminance with low voltage, a wider range of emission wavelengths, rapid response, and reduction in thickness and weight.

Development of novel compounds has been actively pursued to the present because creation of novel compounds is critical in making high-performance organic light-emitting devices. For example, Patent Citations 1 to 4 below describe examples of materials used for emission layers.

Patent Citation 1

Japanese Patent Laid-Open No. 1-289907

Patent Citation 2

Japanese Patent Laid-Open No. 2-247278

Patent Citation 3

Japanese Patent Laid-Open No. 8-113576

Patent Citation 4

Japanese Patent Laid-Open No. 11-12205

DISCLOSURE OF INVENTION

The organic compounds and the organic light-emitting devices that contain the organic compounds described in the above-described patent citations have a room for improvements from the practical viewpoint.

To be more specific, optical output that achieves ever higher luminance and high conversion efficiency are needed for practical application. Moreover, improvements on durability such as changes over time caused by long-term use and deterioration caused by humidity and oxygen-containing ambient gas are needed.

In order for organic light-emitting devices to be applicable to full-color displays and the like, they must achieve blue emission at high color purity and high efficiency, but this has not been satisfactorily achieved.

In view of the above, organic light-emitting devices that achieve high color purity, high emission efficiency, and high durability and materials that can realize such organic light-emitting devices are desired.

In particular, it is desirable to provide a novel organic compound suitable for use in blue light-emitting devices.

An aspect of the present invention provides an organic compound represented by general formula (1):

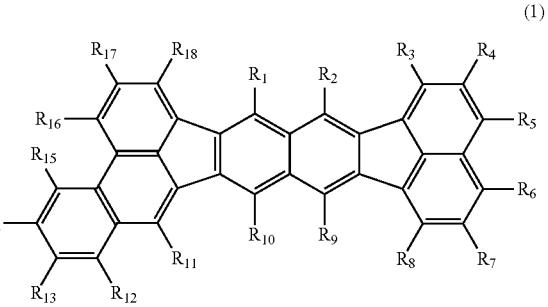

(1)

where $R_1$ to $R_{18}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

The novel organic compound of the present invention can achieve emission at high efficiency and high luminance. Thus, an organic light-emitting device including the novel organic compound of the present invention exhibits high emission efficiency and high luminance.

DESCRIPTION OF EMBODIMENTS

Figure 1:
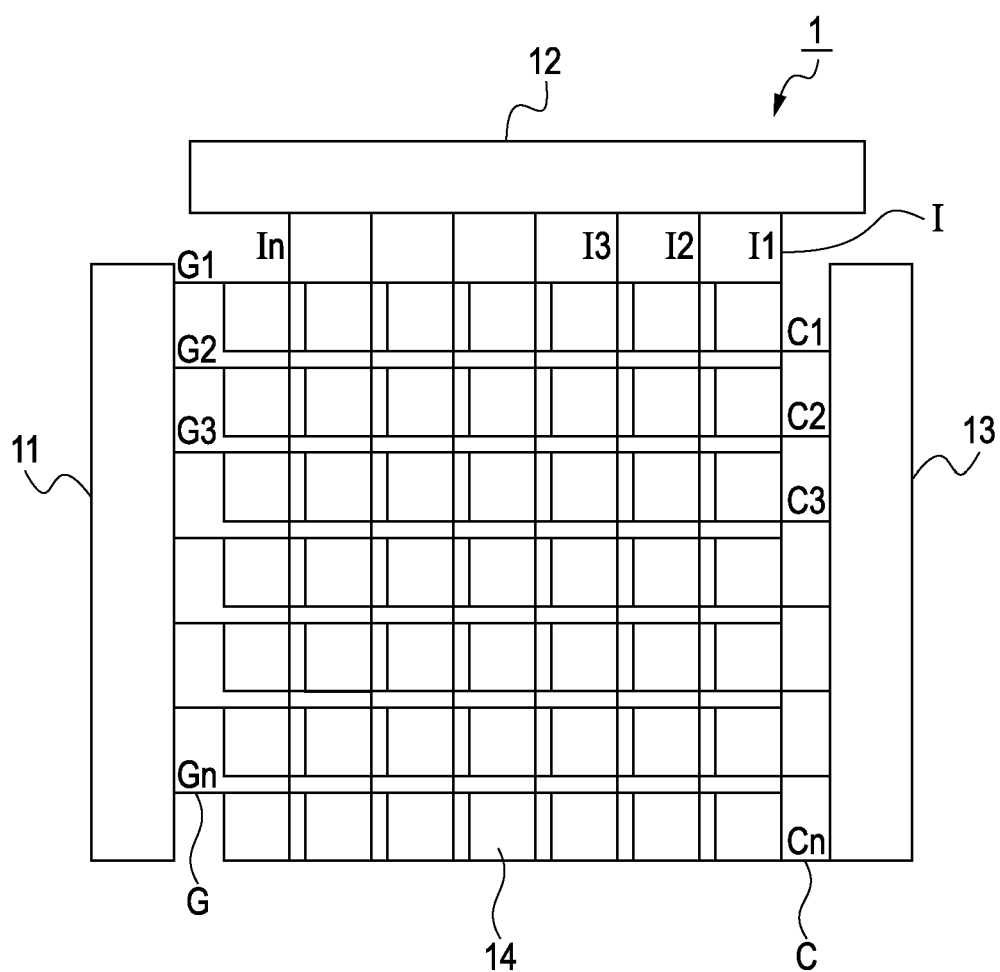
FIG. 1 is a schematic diagram illustrating an organic light-emitting device according to one embodiment and a unit configured to supply electrical signals to the organic light-emitting device.

An organic compound of the present invention is represented by general formula (1) below:

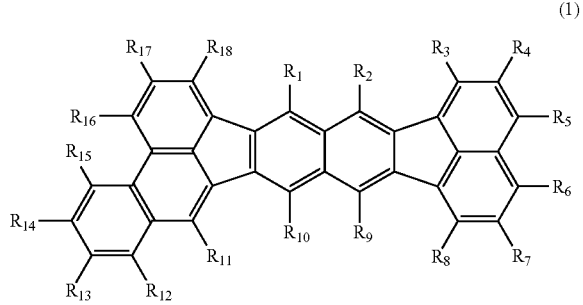

(1)

$R_1$ to $R_{18}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

In formula (1), examples of the alkyl group in the substituted or unsubstituted alkyl group include, but are not limited to, a methyl group, an ethyl group, a normal propyl group, an iso-propyl group, a normal butyl group, a tert-butyl group, a sec-butyl group, an octyl group, a 1-adamantyl group, and a 2-adamantyl group.

In formula (1), examples of the alkoxy group in the substituted or unsubstituted alkoxy group include, but are not limited to, a methoxy group, an ethoxy group, a propoxy group, a 2-ethyl-octyloxy group, a phenoxy group, a 4-tert-butylphenoxy group, a benzyloxy group, and a thienyloxy group.

In formula (1), examples of the amino group in the substituted or unsubstituted amino group include, but are not limited to, an N-methylamino group, an N-ethylamino group, an N,N-dimethylamino group, an N,N-diethylamino group, an N-methyl-N-ethylamino group, an N-benzylamino group, an N-methyl-N-benzylamino group, an N,N-dibenzylamino group, an anilino group, an N,N-diphenylamino group, an N,N-dinaphthylamino group, an N,N-difluorenylamino group, an N-phenyl-N-tolylamino group, an N,N-ditolylamino group, an N-methyl-N-phenylamino group, an N,N-dianisolylamino group, an N-mesityl-N-phenylamino group, an N,N-dimesitylamino group, an N-phenyl-N-(4-tert-butylphenyl)amino group, and an N-phenyl-N-(4-trifluoromethylphenyl)amino group.

In formula (1), examples of the aryl group in the substituted or unsubstituted aryl group include, but are not limited to, a phenyl group, a naphthyl group, an indenyl group, a biphenyl group, a terphenyl group, and a fluorenyl group.

In formula (1), examples of the heterocyclic group in the substituted or unsubstituted heterocyclic group include, but are not limited to, a pyridyl group, an oxazolyl group, an oxadiazolyl group, a thiazolyl group, a thiadiazolyl group, a carbazolyl group, an acridinyl group, and a phenanthrolyl group.

In formula (1), examples of the substituent that may be included in the above-described substituents, namely, the alkyl, alkoxy, amino, aryl, and heterocyclic groups, include, but are not limited to, alkyl groups such as a methyl group, an ethyl group, and a propyl group; aralkyl groups such as a benzyl group; aryl groups such as a phenyl group and a biphenyl group; heterocyclic groups such as a pyridyl group and a pyrrolyl group; amino groups such as a dimethylamino group, a diethylamino group, a dibenzylamino group, a diphenylamino group, and a ditolylamino group; alkoxyl groups such as a methoxyl group, an ethoxyl group, a propoxyl group, and a phenoxyl group; a cyano group; and halogen atoms such as fluorine, chlorine, bromine, and iodine atoms.

Specific examples of the compound represented by general formula (1) are as follows. These examples do not limit the scope of the present invention.

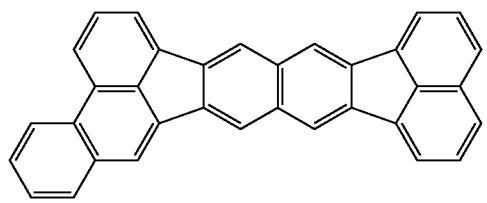

A1

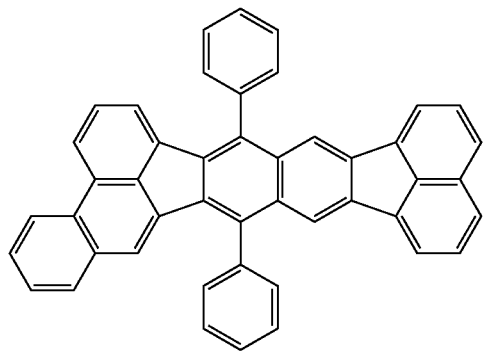

A2

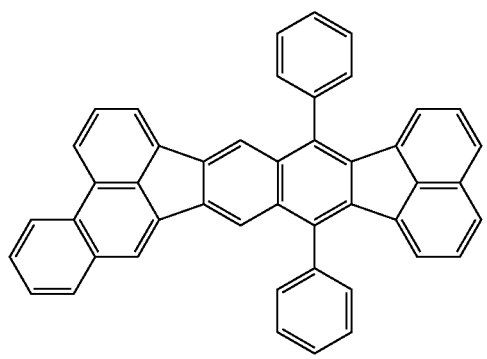

A3

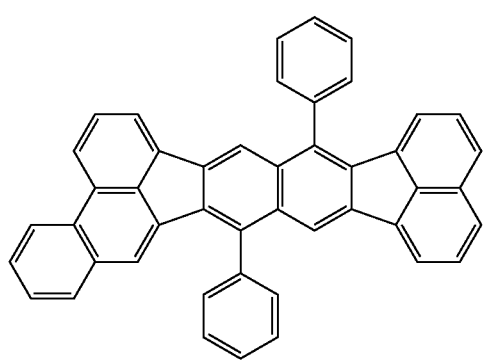

A4

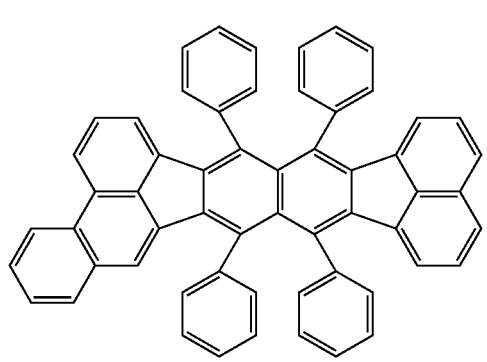

A5

-continued
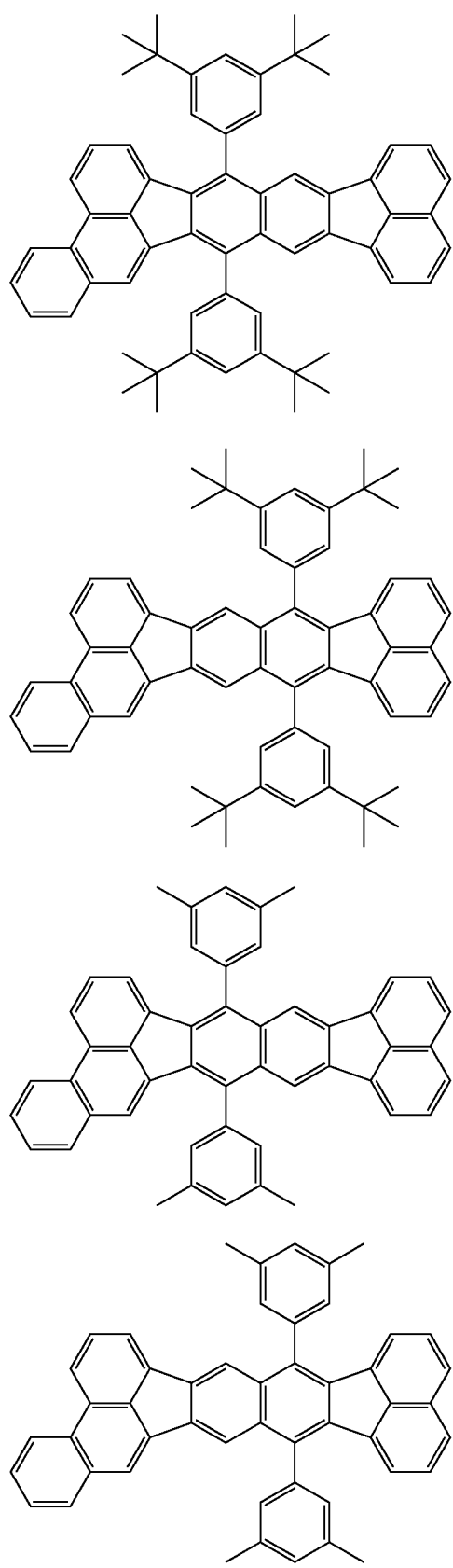
A6
A7
A8
A9
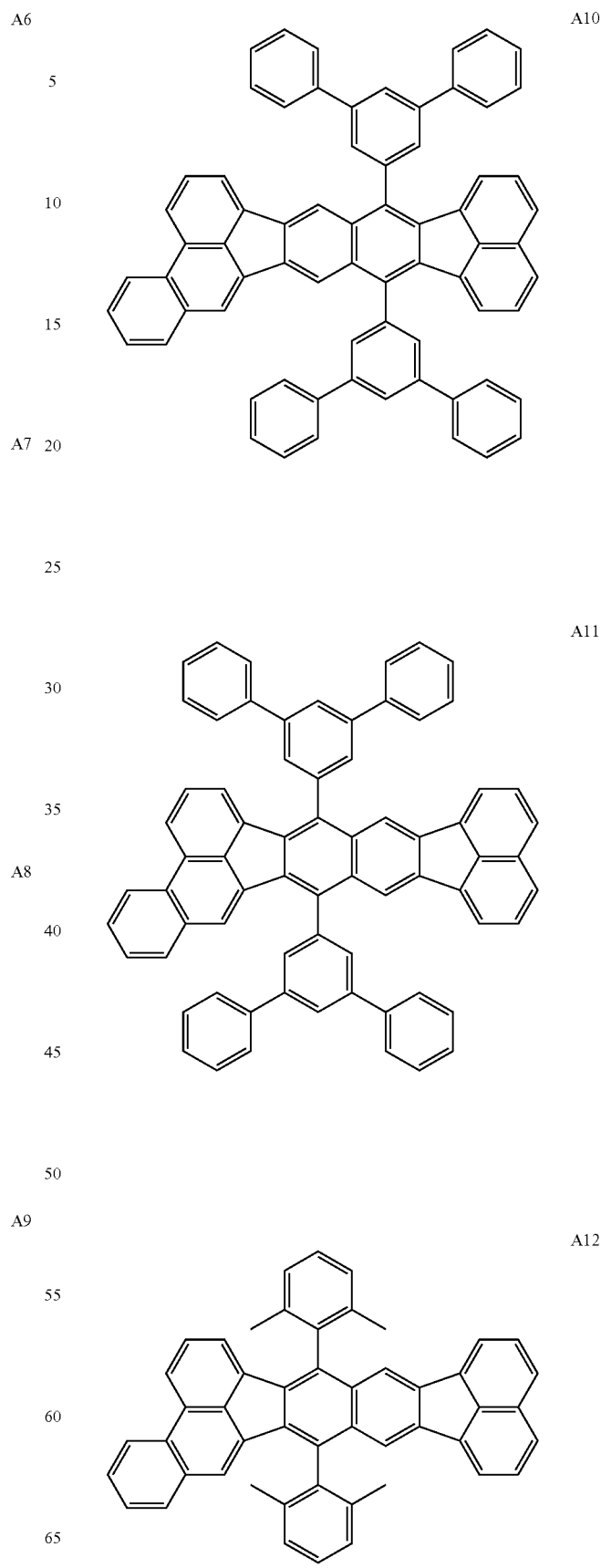
A10
A11
A12

A13
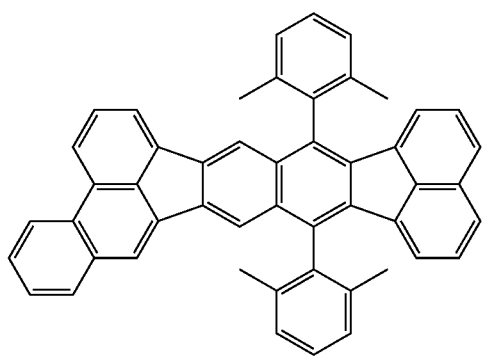
A17
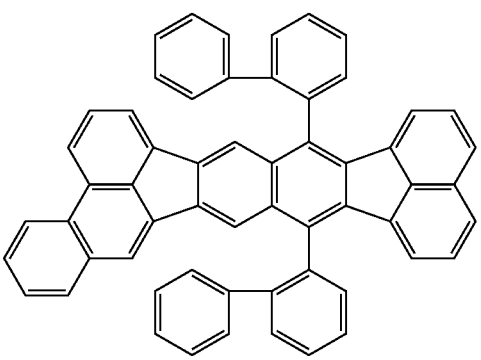
A14
A18
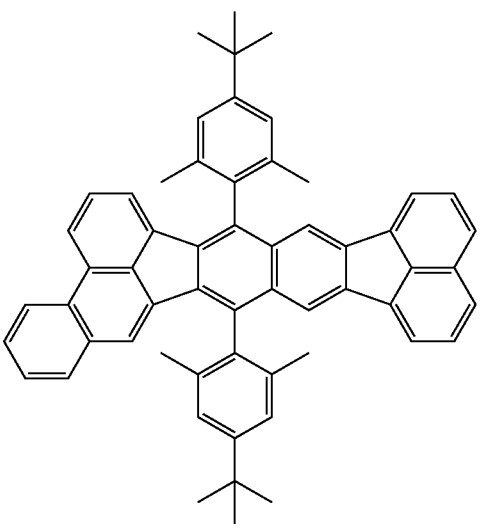
A15
A16
A19
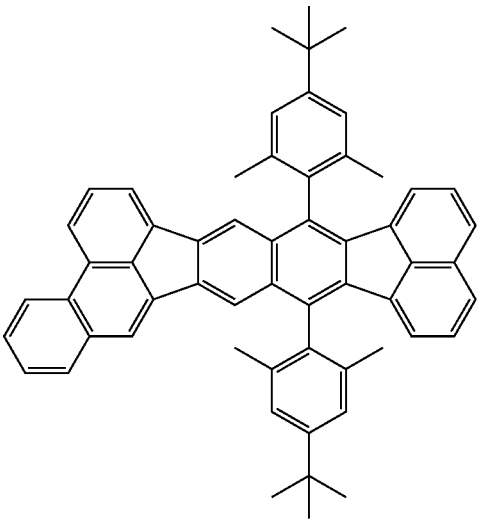

A20
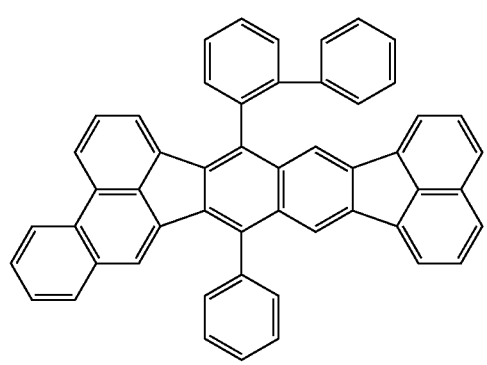
A21
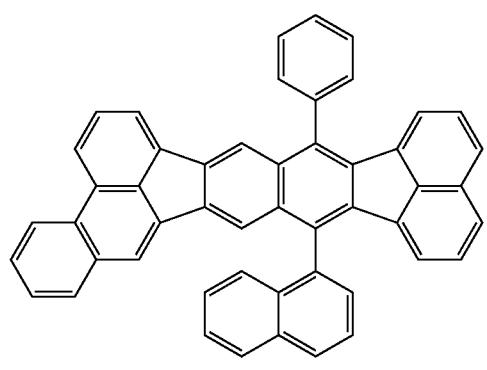
A22
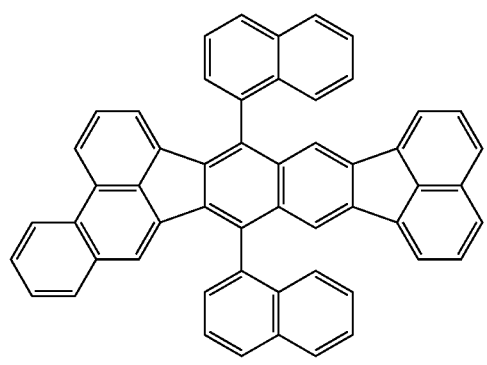
A23
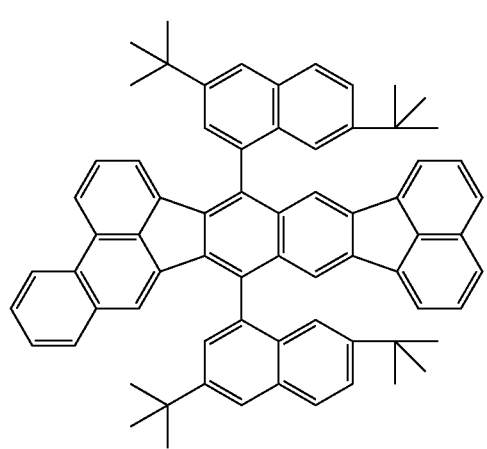
A24
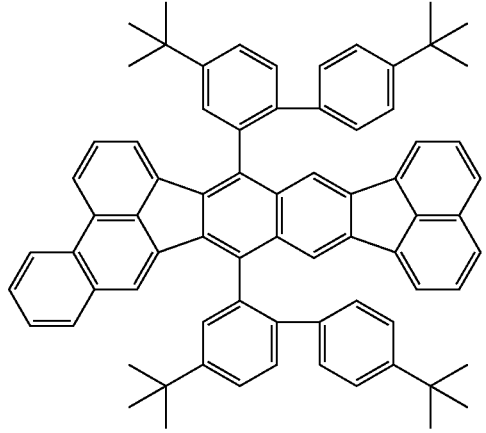
A25
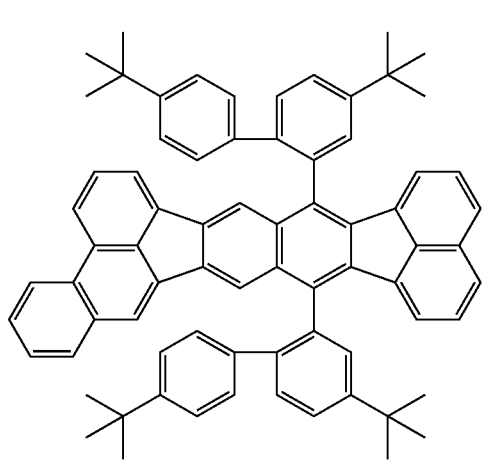
A26
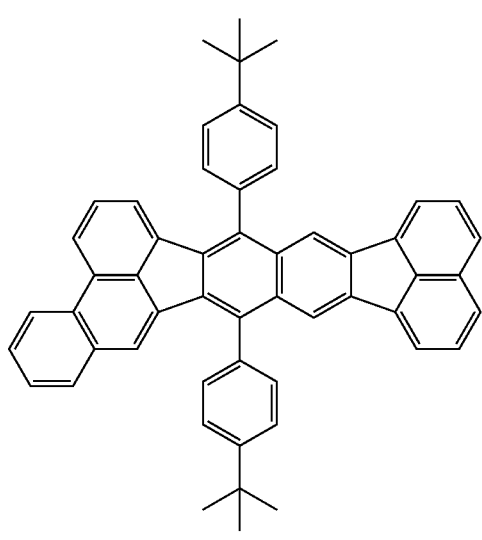

-continued
A27
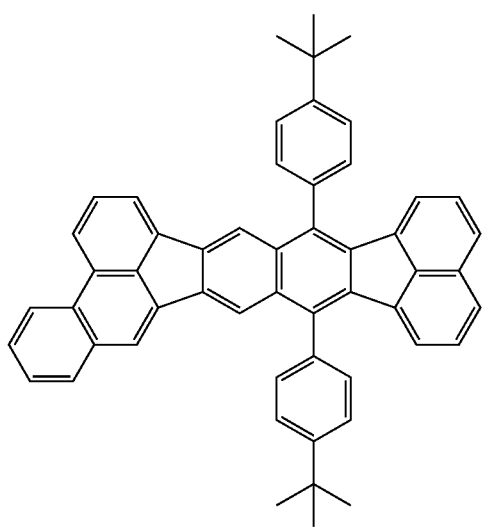
A28
A29
-continued
A30
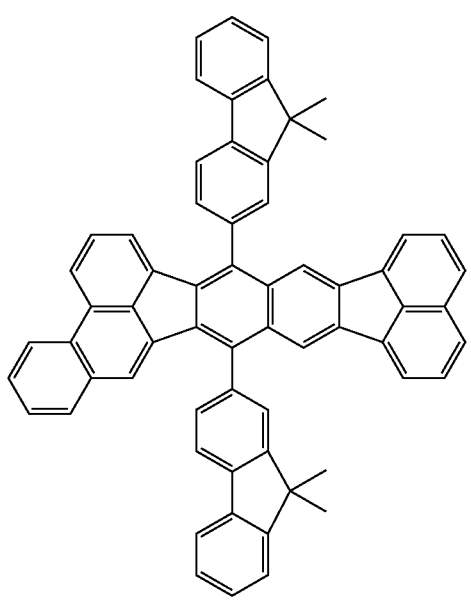
A31
A32

A33
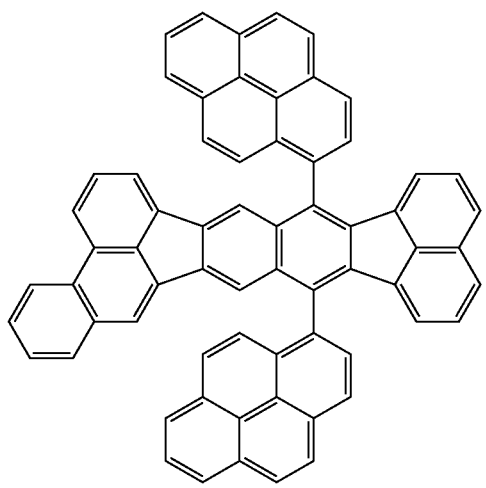
A34
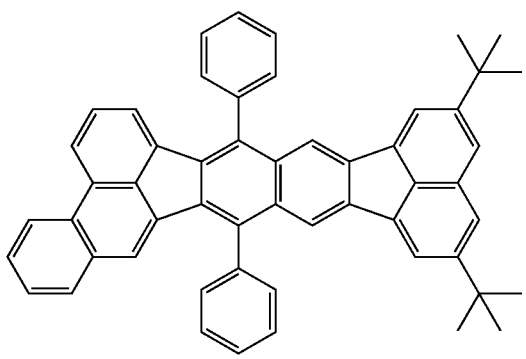
A35
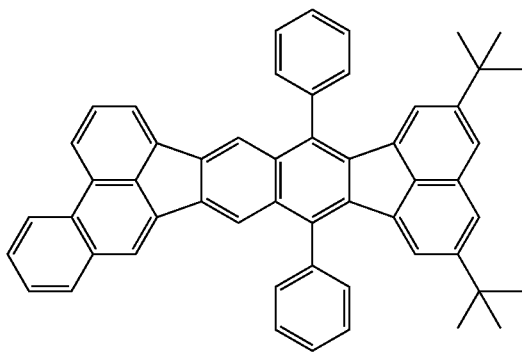
A36
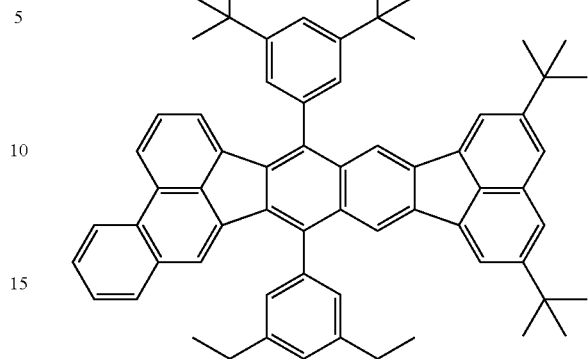
A37
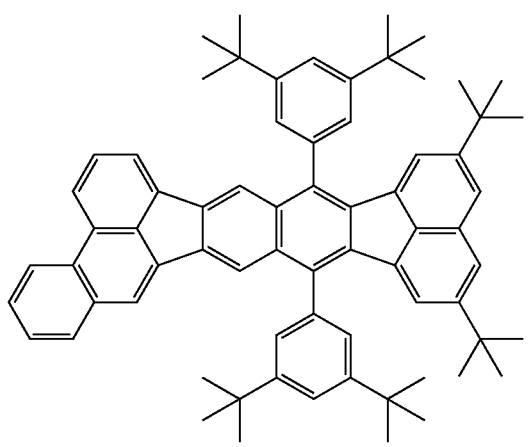
A38
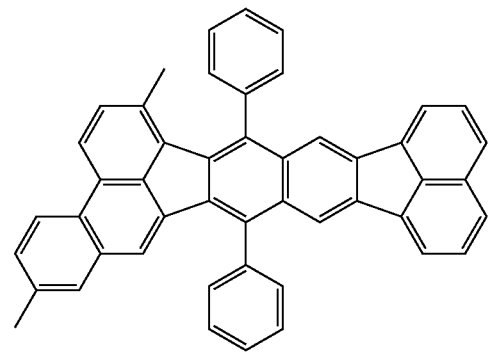
A39
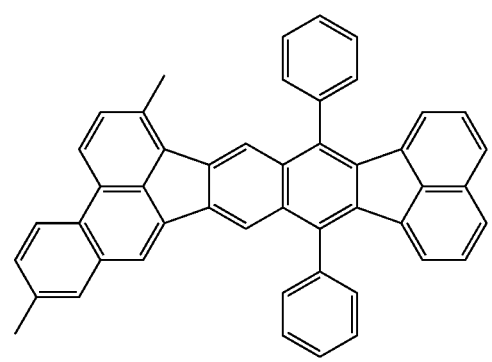

A40
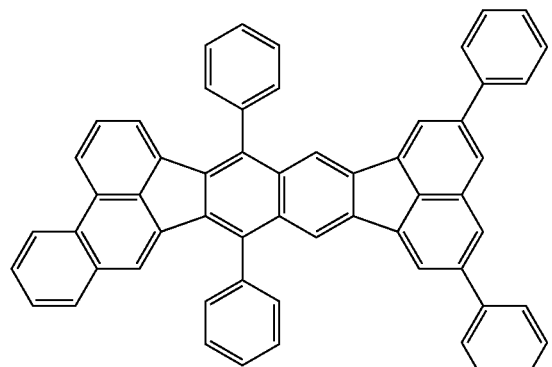
A41
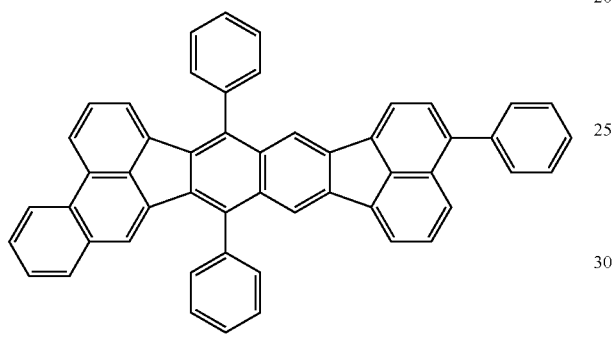
A42
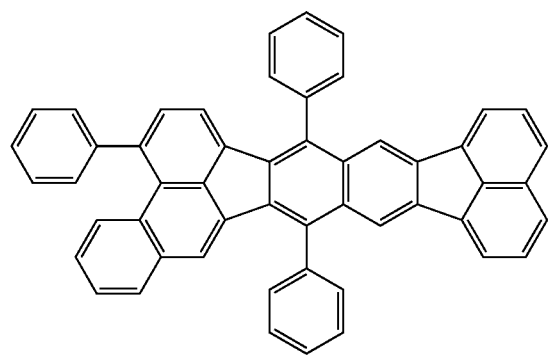
A43
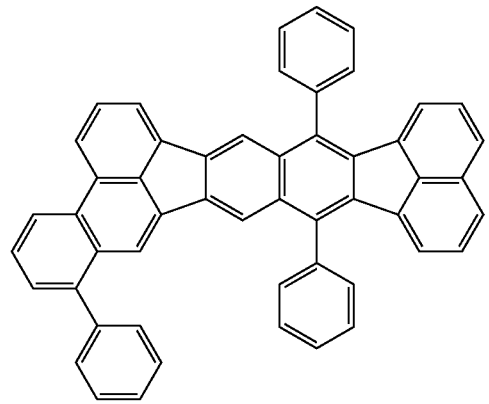
A44
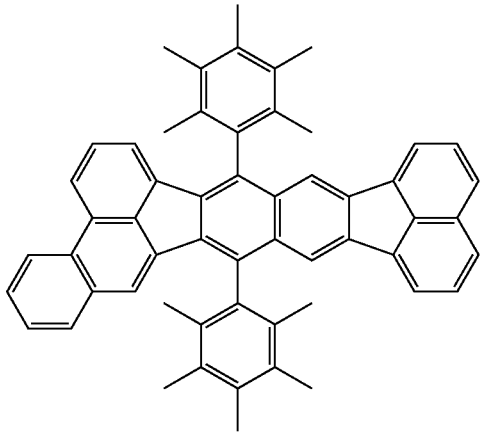
A45
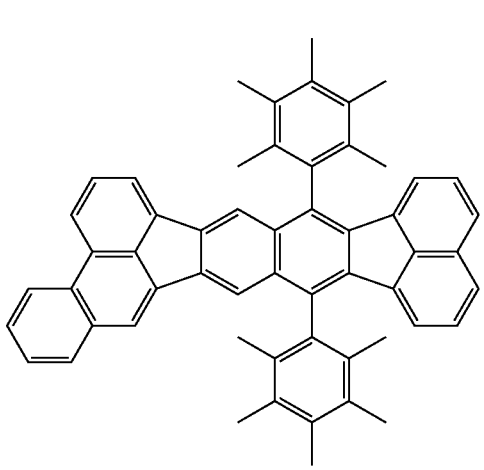
A46
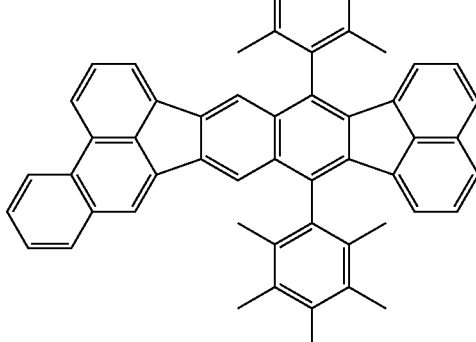

A47
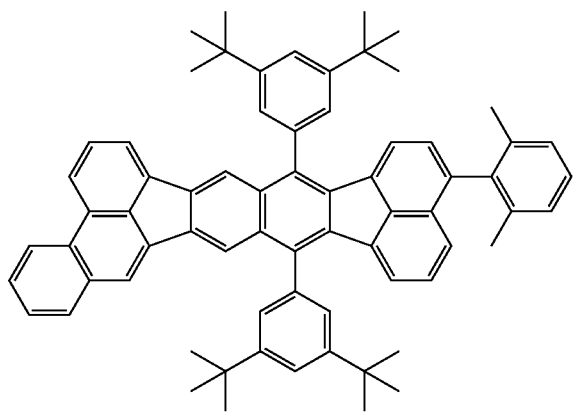
A48
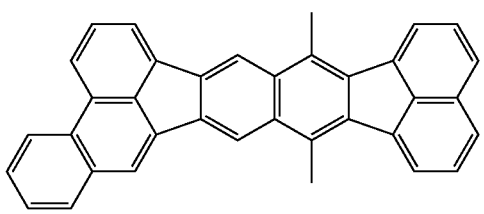
A49
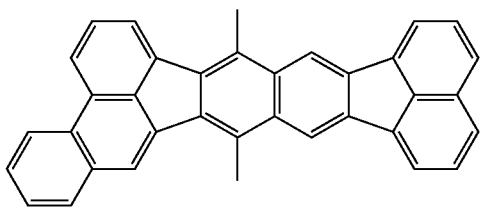
A50
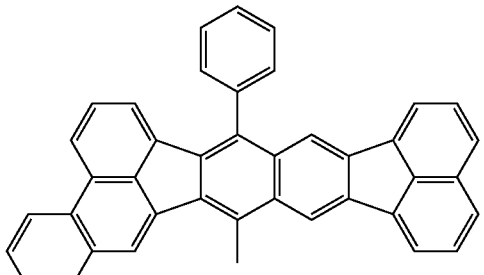
A51
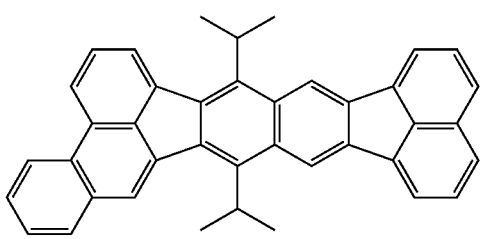
A52
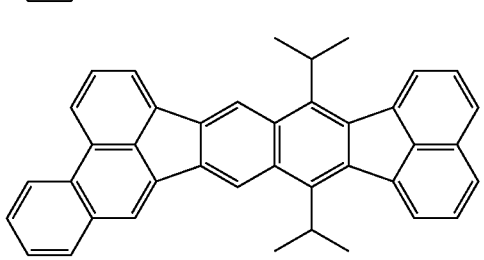
A53
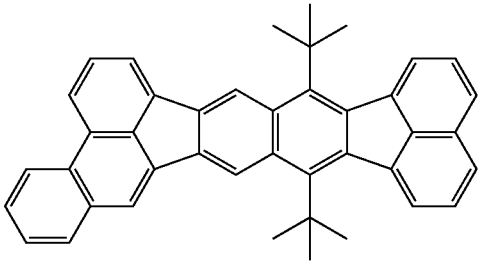
A54
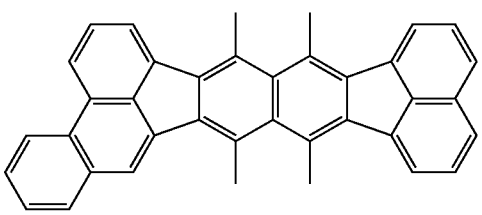
A55
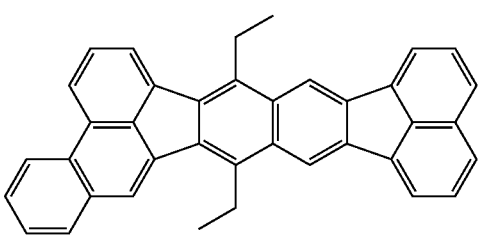
A56
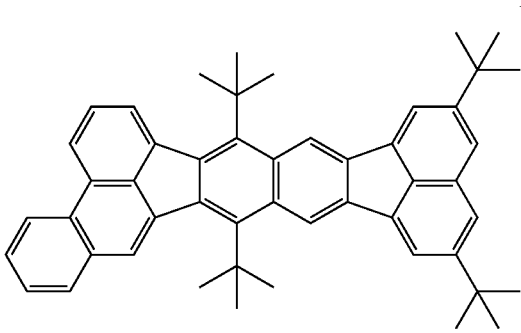
A57
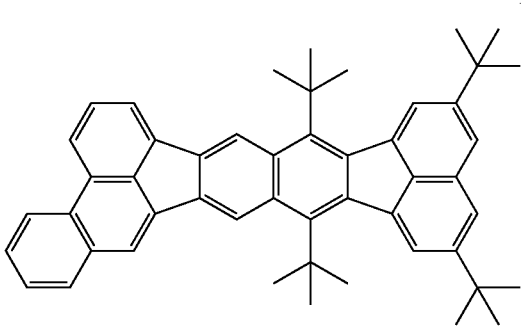

-continued
A58
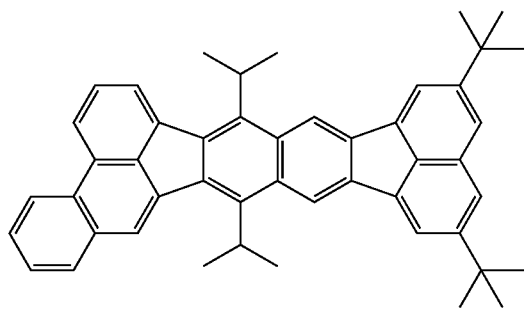
A59
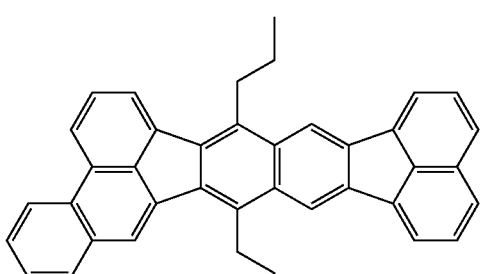
A60
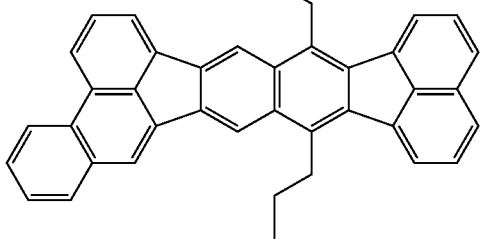
A61
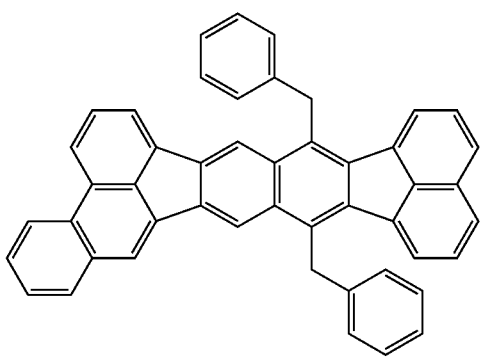
A62
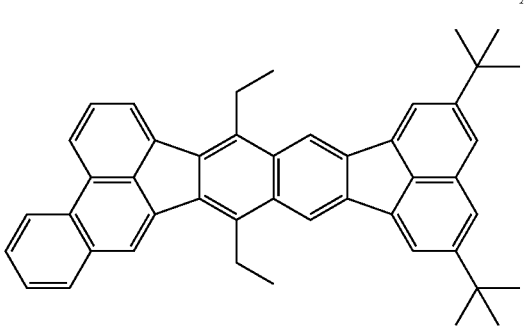
-continued
A63
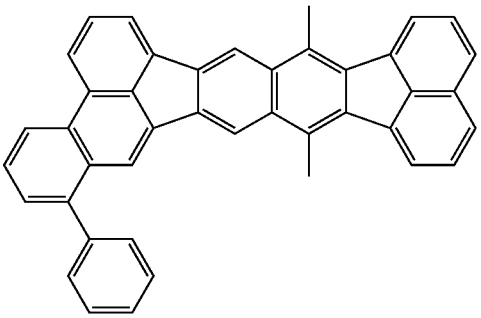
A64
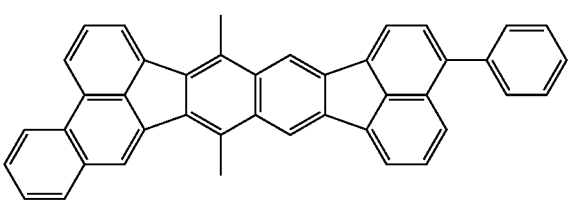
A65
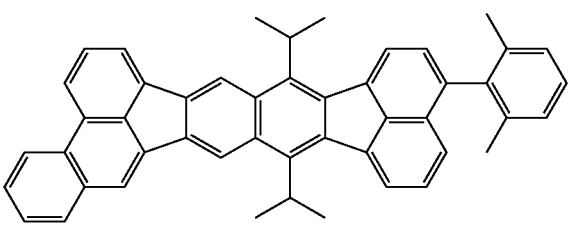
A66
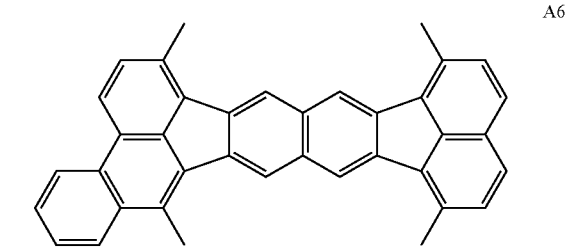
A67
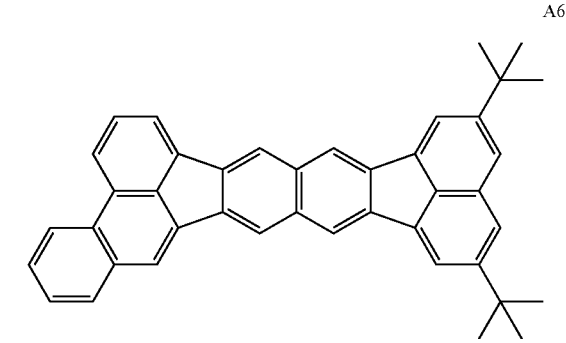
A68
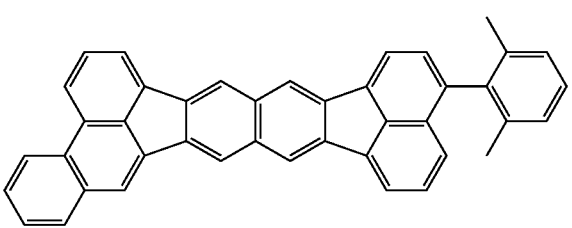

A69
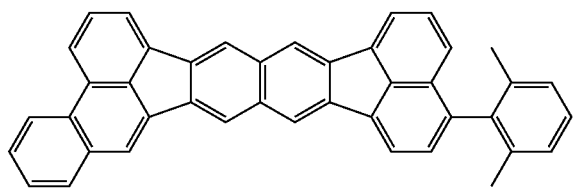
A70
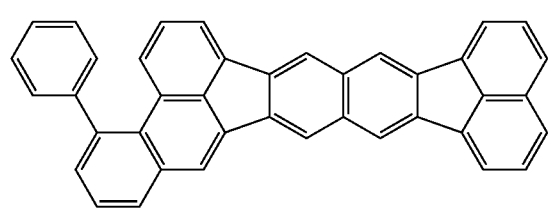
A71
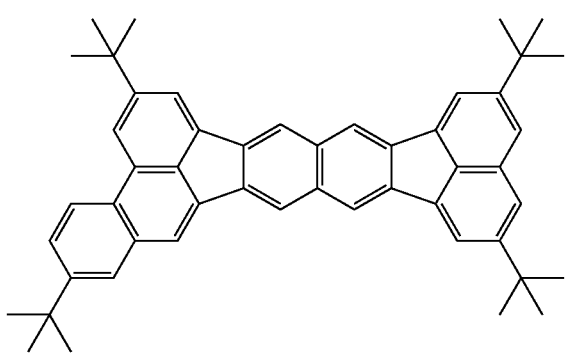
A72
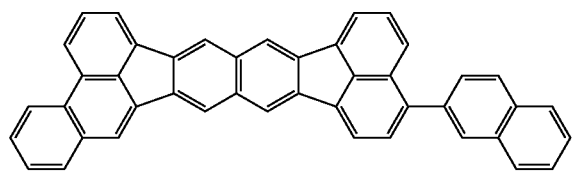
A73
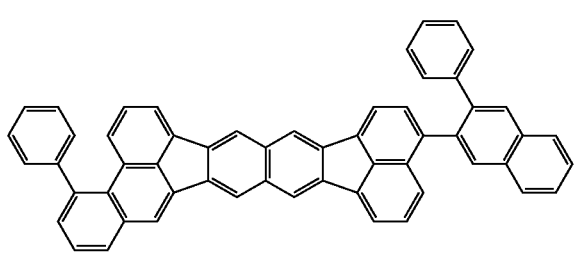
B1
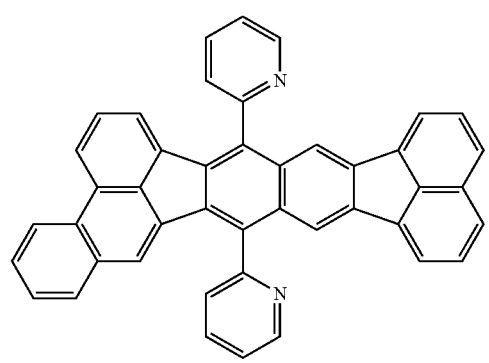
B2
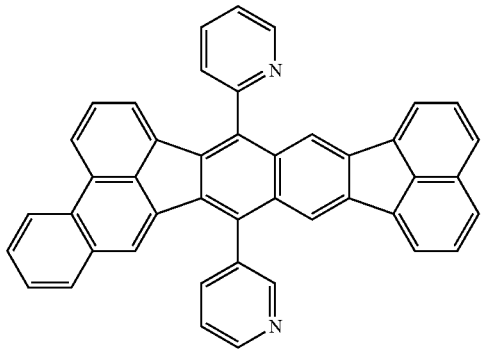
B3
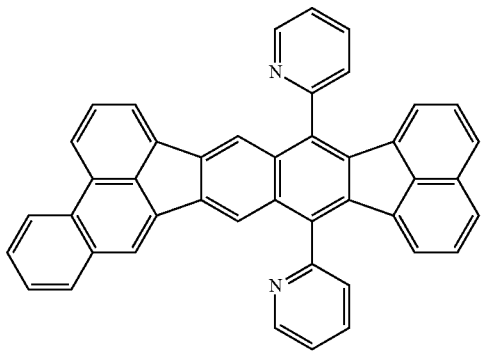
B4
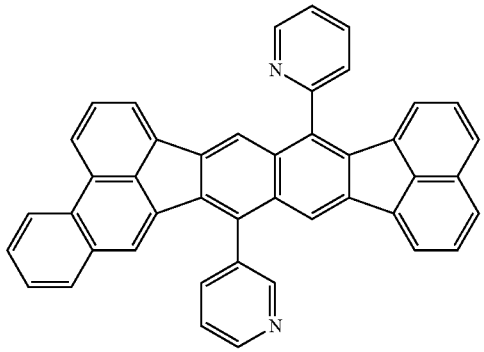
B5
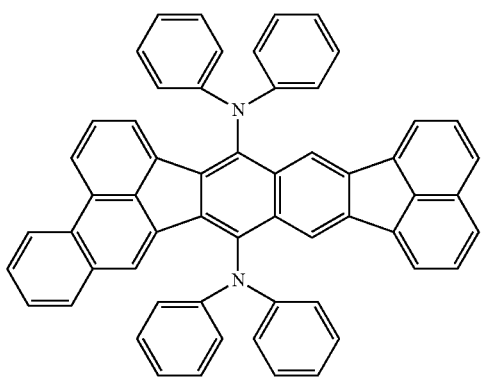

-continued
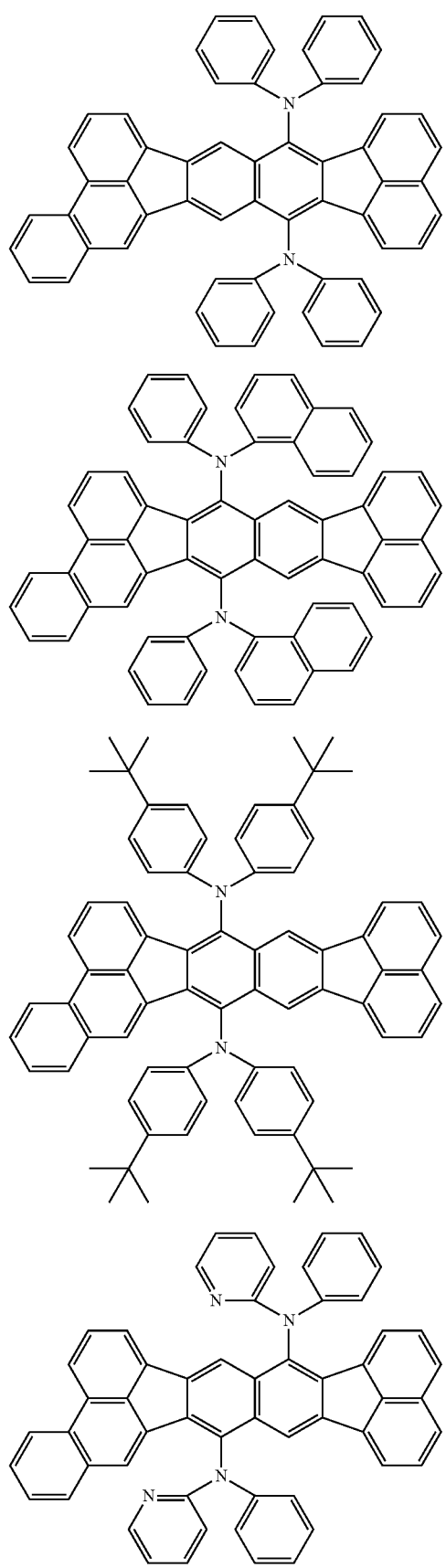
B6
B7
B8
B9
-continued
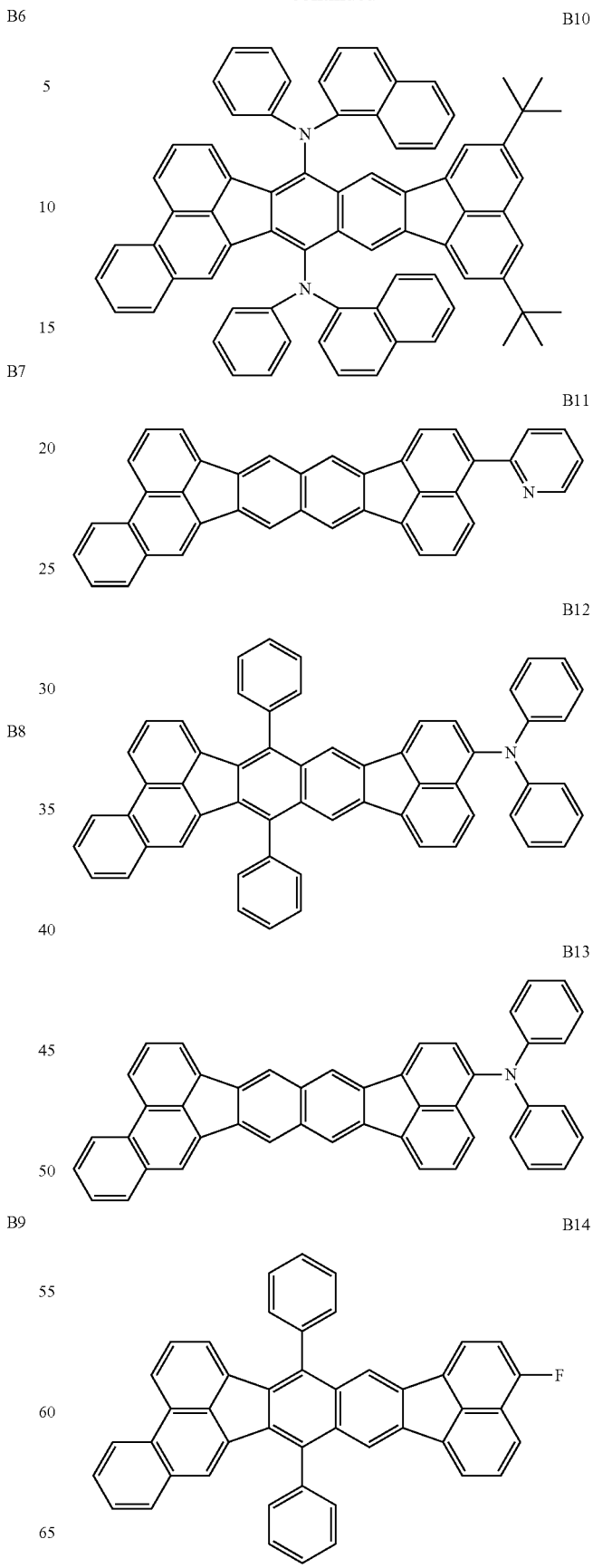
B10
B11
B12
B13
B14

-continued

B15
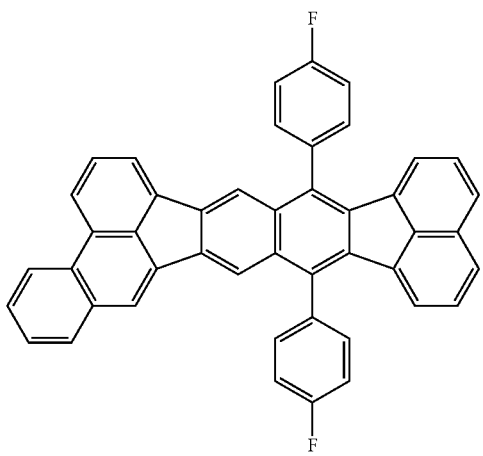

B16
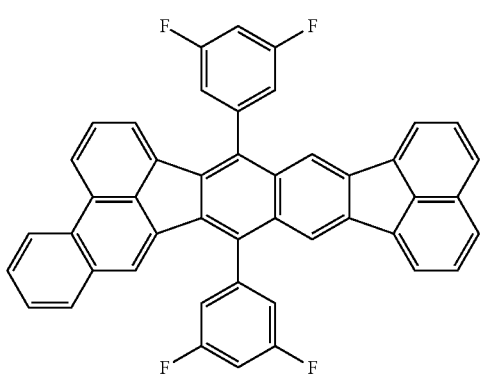

B17
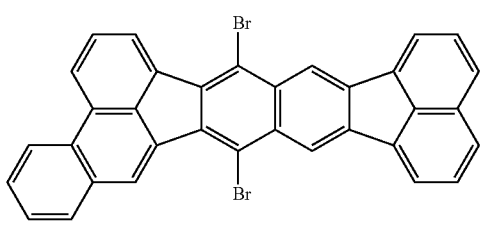

B18
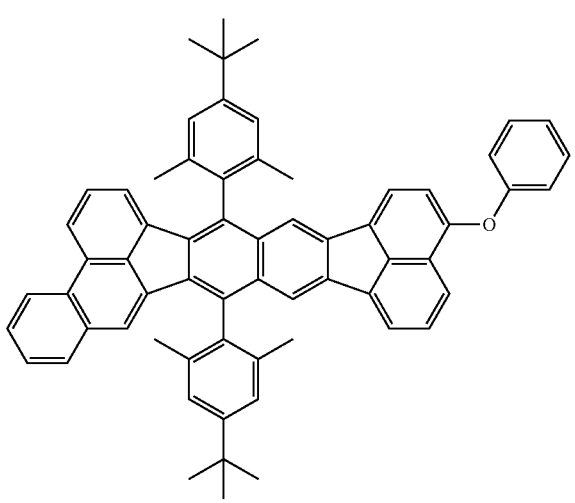

-continued

B19
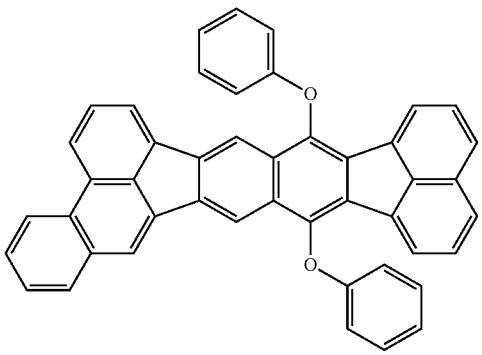

Novel organic compounds of the present invention will now be described in further detail.

In general, in order to increase the emission efficiency of organic light-emitting devices, the emission quantum yield of the emission center material itself is desirably high.

This requires, first, that the oscillator strength be high and, second, that the oscillating portion of the backbone associated with emission be small. These two characteristics should be satisfied simultaneously.

It is important that the blue light-emitting material to be used in image display apparatuses such as organic EL displays have an emission peak in the range of 430 to 480 nm.

With respect to the first characteristic, it is important to enhance the symmetry of the backbone associated with emission from molecules. However, no emission would occur under a forbidden transition condition peculiar to highly symmetrical molecules. The oscillator strength improves as a result of an increased moment of the molecules when the conjugation is extended in the same direction.

With respect to the second characteristic, the decrease in quantum yield resulting from oscillation caused by rotation can be suppressed when the backbone associated with emission is free of any rotational structure.

Figure 5:
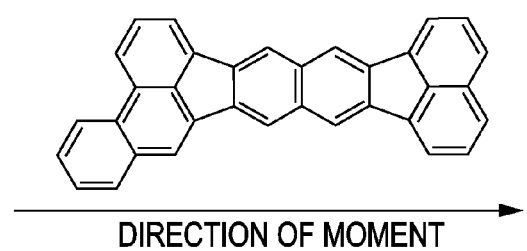
FIG. 5 is a diagram showing a backbone represented by formula (1) and a moment in the X axis direction.

FIG. 5 shows the structure of the backbone of the organic compound of the present invention and the moment in the X axis direction.

In order to achieve a high quantum yield, it is important to increase the moment in the X axis direction as much as possible. However, the wavelength increases if the fused-ring structure is widened to increase the moment. In the organic compound of the present invention, the molecule is made slightly asymmetric as shown in FIG. 5 to achieve a high quantum yield while increasing the moment in the X axis direction and widening the fused ring structure without increasing the wavelength. As a result, it has been found that a high emission quantum yield can be obtained within the blue emission range.

Moreover, since the backbone of the organic compound of the present invention shown in FIG. 5 has no rotational structure, the decrease in quantum yield by rotation oscillation can be suppressed.

Table 1 below shows the results of quantum chemical calculation at the B3LYP/6-31G* level using a density functional theory. The organic compound of the present invention has a high oscillator strength attributable to its structure as shown in the left column of Table 1 below. The compound at the middle and the compound on the right-hand side of Table 1 are reference examples. Among the reference examples, the compound on the right-hand side has one less fused ring than the backbone of the organic compound of the present invention. As a result, the oscillator strength is lower than that of the backbone of the organic compound of the present invention.

TABLE 1

| Structural formula | | | |
|---|---|---|---|
| Oscillator strength | 0.524 | 0.018 | 0.491 |

Since two five-membered rings are included in the backbone, the organic compound of the present invention has a low HOMO-LUMO energy level and is stable against oxidation. When the organic compound is used as a light-emitting material, it is suitable as an electron-trapping light-emitting material.

The organic compound of the present invention has a high planarity and easily generate excimers when it is unsubstituted.

In order to suppress generation of excimers, a substituent such as a phenyl group or an alkyl group can be introduced into R1, R2, R9, and/or R10 of the naphthalene backbone at the center of the organic compound of the present invention. In particular, when a phenyl group is introduced, the phenyl group is orthogonally arranged to the backbone, thereby rendering the structure three-dimensional. Thus, stacking of molecules can be suppressed and concentration quenching can be suppressed. Here, "orthogonally arranged" means that the plane of the phenyl group is orthogonal to the plane of benzofluoranthene.

The position into which the substituent is introduced is not particularly limited.

In order to prevent basic physical properties of the backbone from changing significantly, the substituent is preferably a hydrocarbon. However, in changing the HOMO-LUMO level, i.e., in significantly changing the color of emission from the organic compound from blue to green or red (i.e., in order to increase the wavelength), a substituent that includes a heteroatom should be introduced.

Organic compounds represented by general formula (1) can be synthesized through the following synthetic route 1 or 2 with reference to literature, Journal of Organic Chemistry (1952), 17 845-54, Journal of the American Chemical Society (1952), 74 1075-1076, or Journal of Organic Chemistry (2003), 68, 883-887. As for the substituent, various types of substituents are introduced. For example, synthesis can be conducted by substituting hydrogen atoms with other substituents, such as an alkyl group, a halogen atom, and a phenyl group.

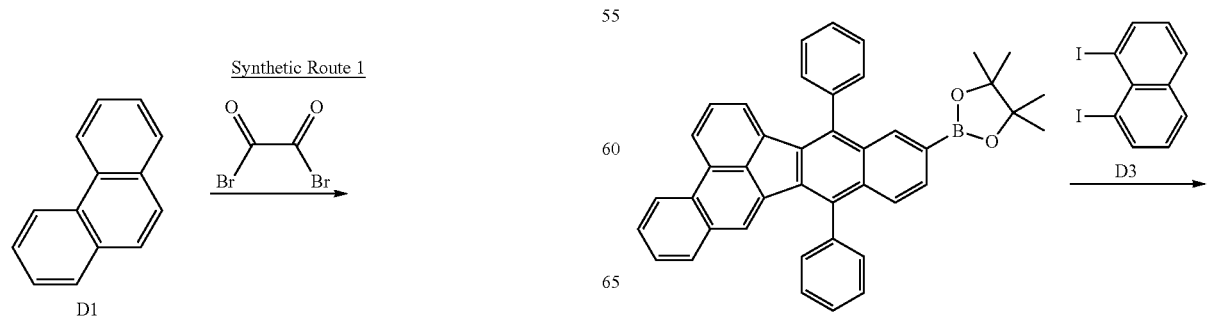

-continued

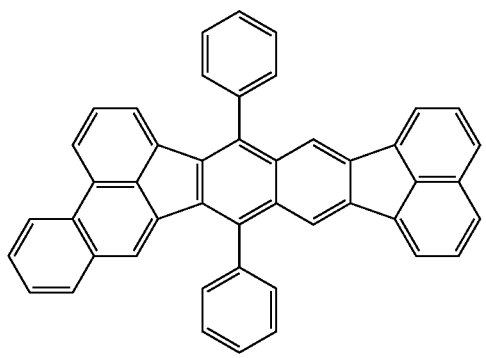

Synthetic Route 2

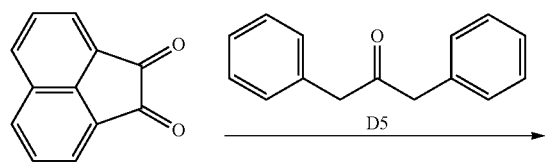

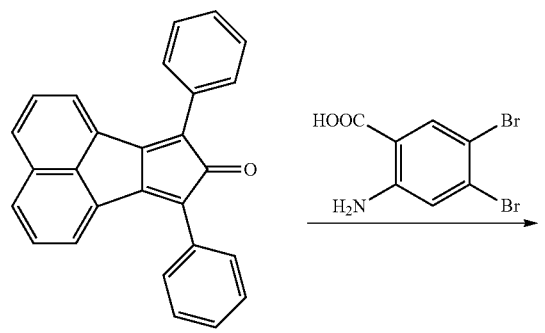

-continued

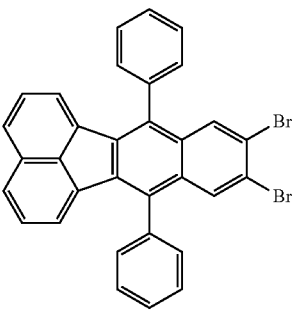

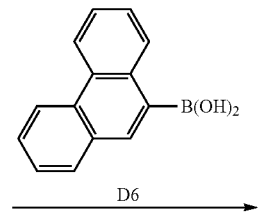

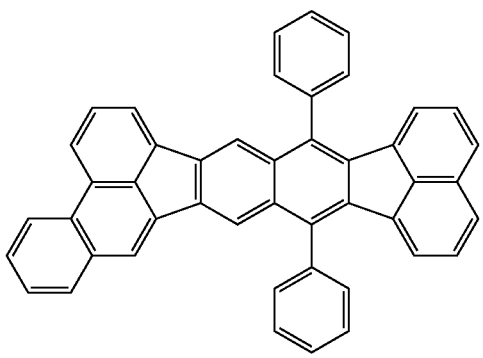

Various organic compounds of the present invention can be synthesized from starting materials D1 or D4, D2 or D5, and D3 or D6. Organic compounds (synthetic compounds) that can be synthesized are shown in Tables 2 and 3. Tables 2 and 3 also indicate the starting materials of these compounds. The starting materials of each synthetic example are indicated as D1 or D4, D2 or D5, and D3 or D6 in Tables 2 and 3.

TABLE 2

| | D1 or D4 | D2 or D5 |
|---|---|---|
| Synthetic Example 1 | 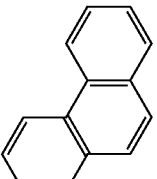 | 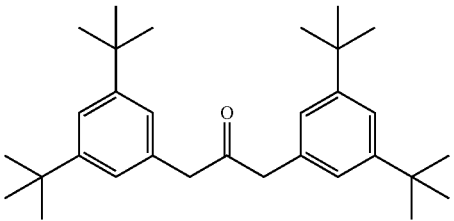 [SMILES: CC(C)(C)c1cc(CC(=O)Cc2cc(C(C)(C)C)cc(C(C)(C)C)c2)cc(C(C)(C)C)c1] |
| Synthetic Example 2 | 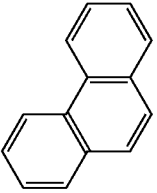 [SMILES: c1ccc2c(c1)ccc1ccccc12] | 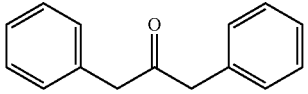 [SMILES: O=C(Cc1ccccc1)Cc1ccccc1] |

TABLE 2-continued
| | | |
|---|---|---|
| Synthetic Example 3 | 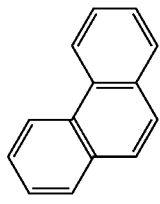 [SMILES: c1ccc2c(c1)ccc1ccccc12] | 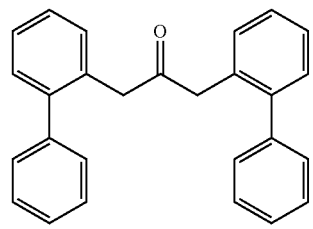 [SMILES: O=C(Cc1ccccc1-c1ccccc1)Cc1ccccc1-c1ccccc1] |
| Synthetic Example 4 | 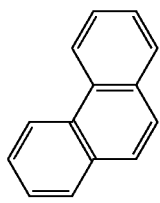 [SMILES: c1ccc2c(c1)ccc1ccccc12] | 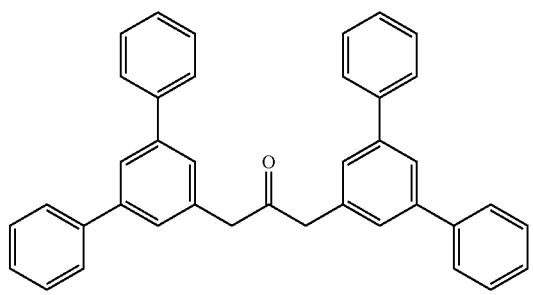 [SMILES: O=C(Cc1cc(-c2ccccc2)cc(-c2ccccc2)c1)Cc1cc(-c2ccccc2)cc(-c2ccccc2)c1] |
| Synthetic Example 5 | 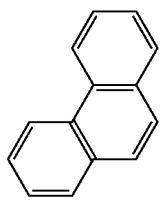 [SMILES: c1ccc2c(c1)ccc1ccccc12] | 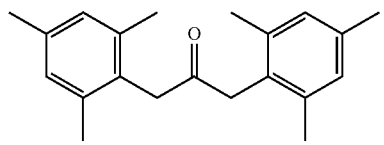 |
| Synthetic Example 6 | 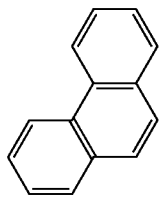 [SMILES: c1ccc2c(c1)ccc1ccccc12] | 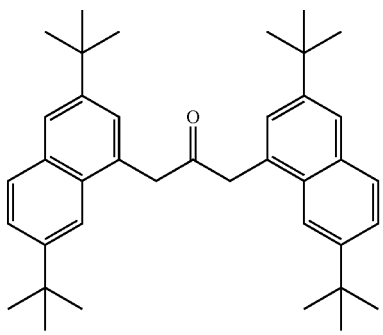 [SMILES: CC(C)(C)c1cc(CC(=O)Cc2cc(C(C)(C)C)cc3ccc(C(C)(C)C)cc23)c2cc(C(C)(C)C)ccc2c1] |
| Synthetic Example 7 | 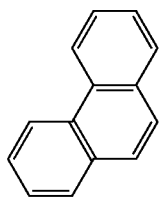 [SMILES: c1ccc2c(c1)ccc1ccccc12] | 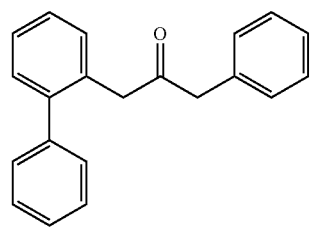 [SMILES: O=C(Cc1ccccc1)Cc1ccccc1-c1ccccc1] |
| Synthetic Example 8 | 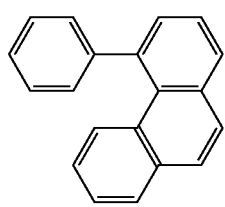 [SMILES: c1ccc(-c2cccc3ccc4ccccc4c23)cc1] | 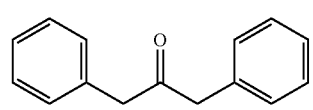 [SMILES: O=C(Cc1ccccc1)Cc1ccccc1] |

TABLE 2-continued
| | | |
|---|---|---|
| Synthetic Example 9 | 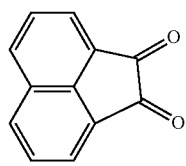 [SMILES: O=C1C(=O)c2cccc3cccc1c23] | 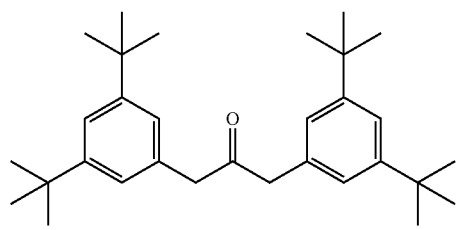 [SMILES: CC(C)(C)c1cc(CC(=O)Cc2cc(C(C)(C)C)cc(C(C)(C)C)c2)cc(C(C)(C)C)c1] |
| Synthetic Example 10 | 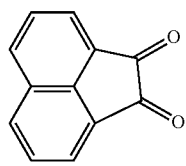 [SMILES: O=C1C(=O)c2cccc3cccc1c23] | 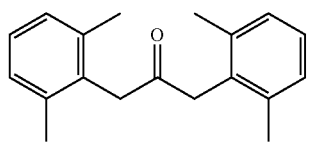 [SMILES: Cc1cccc(C)c1CC(=O)Cc1c(C)cccc1C] |
| D3 or D6 | Synthetic compounds |
|---|---|
| Synthetic Example 1 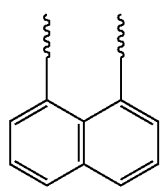 | 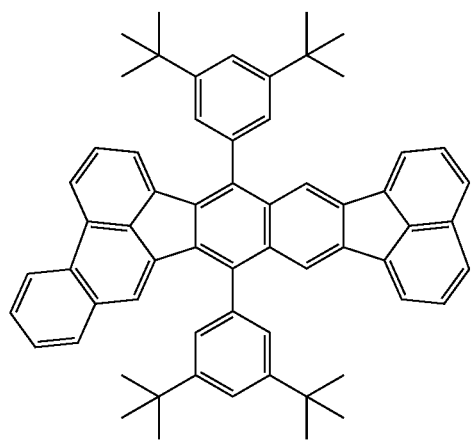 [SMILES: CC(C)(C)c1cc(-c2c3cc4c(cc3c(-c3cc(C(C)(C)C)cc(C(C)(C)C)c3)c3c5cc6ccccc6c6cccc(c23)c65)c2cccc3cccc4c32)cc(C(C)(C)C)c1] |
| Synthetic Example 2 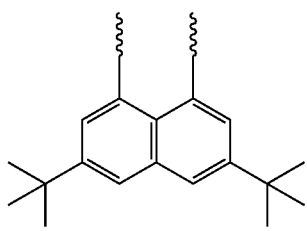 | 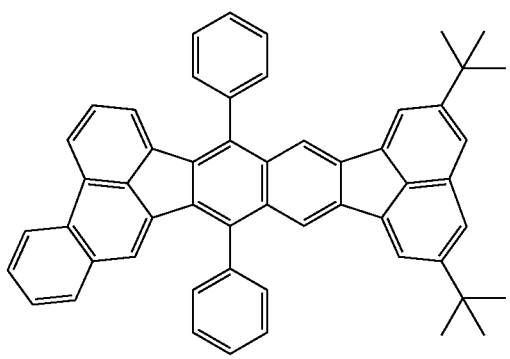 [SMILES: CC(C)(C)c1cc2cc(C(C)(C)C)cc3c4cc5c(-c6ccccc6)c6c7cc8ccccc8c8cccc(c6c(-c6ccccc6)c5cc4c(c1)c23)c87] |
| Synthetic Example 3 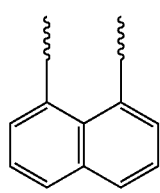 | 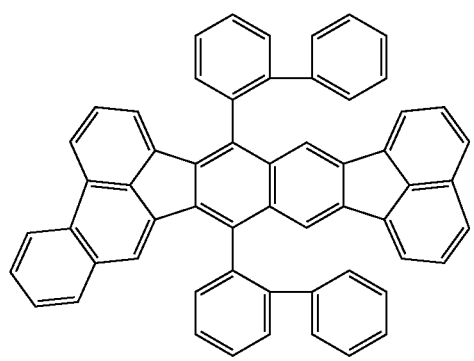 [SMILES: c1ccc(-c2ccccc2-c2c3cc4c(cc3c(-c3ccccc3-c3ccccc3)c3c5cc6ccccc6c6cccc(c23)c65)c2cccc3cccc4c32)cc1] |

TABLE 2-continued
Synthetic Example 4 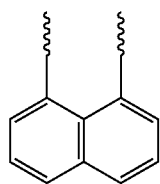 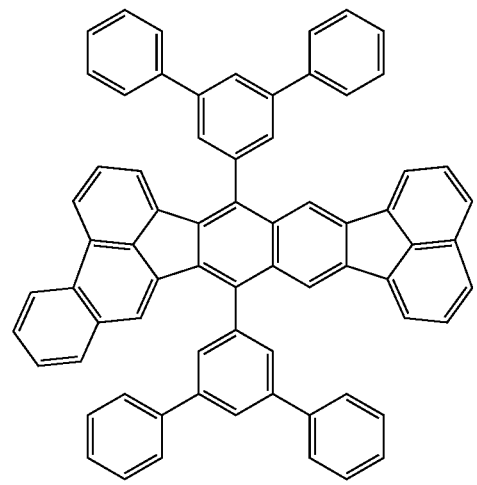 [SMILES: c1ccc(-c2cc(-c3ccccc3)cc(-c3c4cc5c(cc4c(-c4cc(-c6ccccc6)cc(-c6ccccc6)c4)c4c6cc7ccccc7c7cccc(c34)c76)c3cccc4cccc5c43)c2)cc1]
Synthetic Example 5 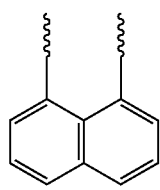 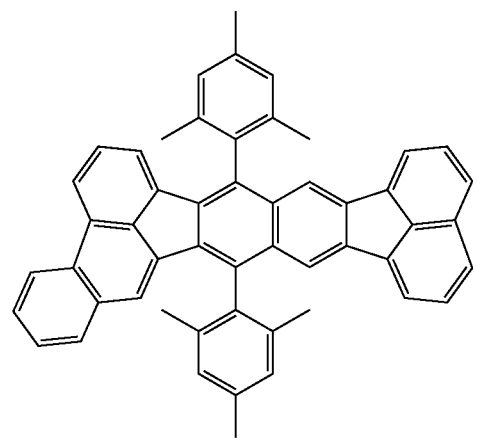 [SMILES: Cc1cc(C)c(-c2c3cc4c(cc3c(-c3c(C)cc(C)cc3C)c3c5cc6ccccc6c6cccc(c23)c65)c2cccc3cccc4c32)c(C)c1]
Synthetic Example 6 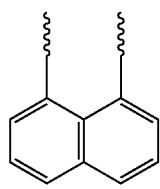 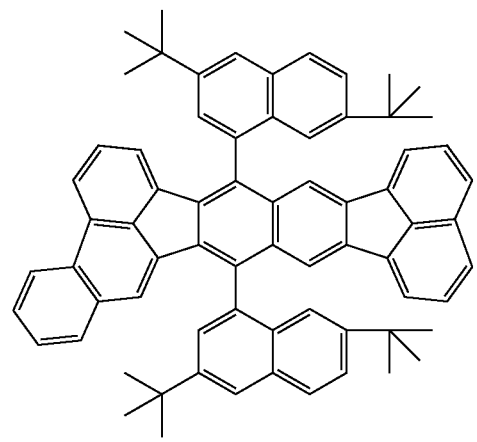 [SMILES: CC(C)(C)c1cc(-c2c3cc4c(cc3c(-c3cc(C(C)(C)C)cc5ccc(C(C)(C)C)cc35)c3c5cc6ccccc6c6cccc(c23)c65)c2cccc3cccc4c32)c2cc(C(C)(C)C)ccc2c1]

TABLE 2-continued
| | | |
|---|---|---|
| Synthetic Example 7 | 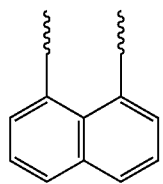 | 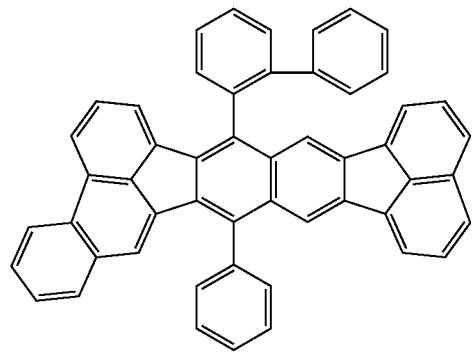 [SMILES: c1ccc(-c2ccccc2-c2c3cc4c(cc3c(-c3ccccc3)c3c5cc6ccccc6c6cccc(c23)c65)c2cccc3cccc4c32)cc1] |
| Synthetic Example 8 | 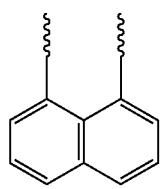 | 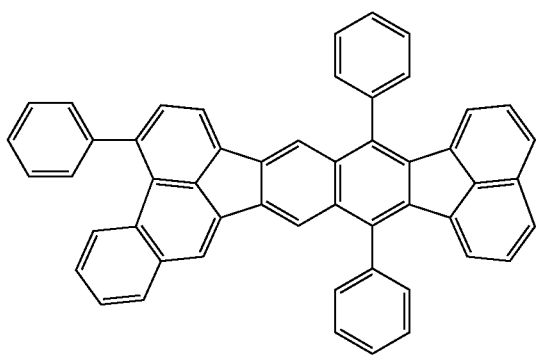 [SMILES: c1ccc(-c2c3cc4c(cc3c(-c3ccccc3)c3c5cccc6cccc(c23)c65)c2cc3ccccc3c3c(-c5ccccc5)ccc4c23)cc1] |
| Synthetic Example 9 | 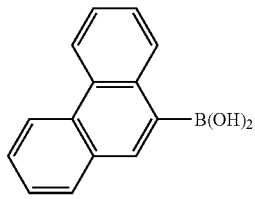 [SMILES: OB(O)c1cc2ccccc2c2ccccc12] | 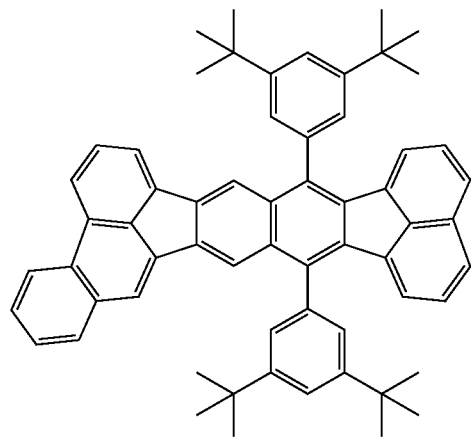 [SMILES: CC(C)(C)c1cc(-c2c3cc4c(cc3c(-c3cc(C(C)(C)C)cc(C(C)(C)C)c3)c3c5cccc6cccc(c23)c65)c2cc3ccccc3c3cccc4c32)cc(C(C)(C)C)c1] |
| Synthetic Example 10 | 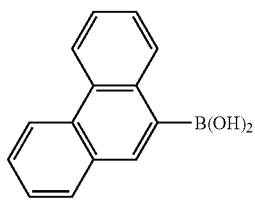 [SMILES: OB(O)c1cc2ccccc2c2ccccc12] | 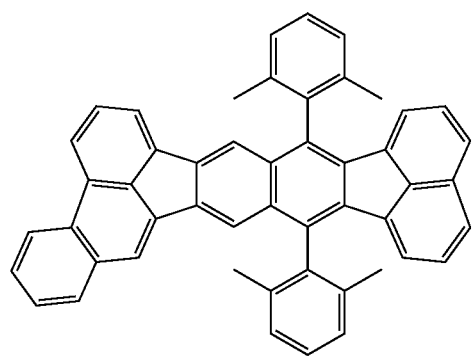 [SMILES: Cc1cccc(C)c1-c1c2cc3c(cc2c(-c2c(C)cccc2C)c2c4cccc5cccc(c12)c54)c1cc2ccccc2c2cccc3c21] |

TABLE 3

| | D1 or D4 | D2 or D5 |
|---|---|---|
| Synthetic Example 11 | | |
| Synthetic Example 12 | | |
| Synthetic Example 13 | | |
| Synthetic Example 14 | | |
| Synthetic Example 15 | | |
| Synthetic Example 16 | | |

TABLE 3-continued
| D3 or D6 | Synthetic compounds |
|---|---|
| Synthetic Example 11 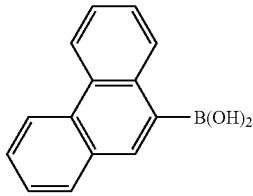 [SMILES: OB(O)c1cc2ccccc2c2ccccc12] | 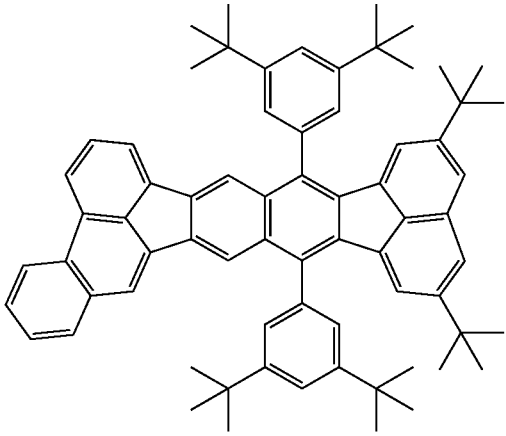 [SMILES: CC(C)(C)c1cc(-c2c3cc4c(cc3c(-c3cc(C(C)(C)C)cc(C(C)(C)C)c3)c3c5cc(C(C)(C)C)cc6cc(C(C)(C)C)cc(c23)c65)c2cc3ccccc3c3cccc4c32)cc(C(C)(C)C)c1] |
| Synthetic Example 12 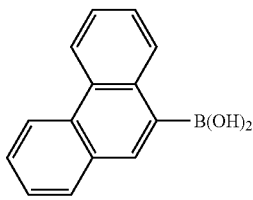 [SMILES: OB(O)c1cc2ccccc2c2ccccc12] | 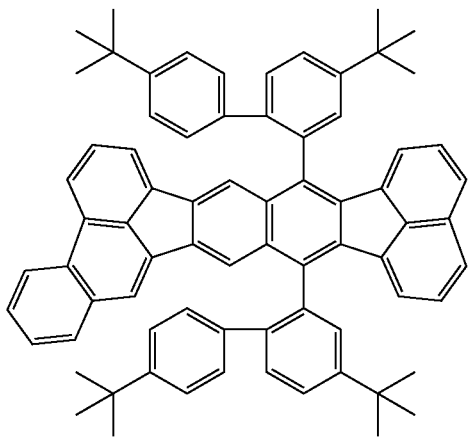 [SMILES: CC(C)(C)c1ccc(-c2ccc(C(C)(C)C)cc2-c2c3cc4c(cc3c(-c3cc(C(C)(C)C)ccc3-c3ccc(C(C)(C)C)cc3)c3c5cccc6cccc(c23)c65)c2cc3ccccc3c3cccc4c32)cc1] |
| Synthetic Example 13 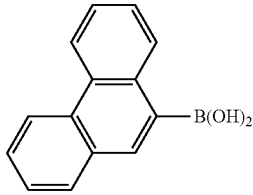 [SMILES: OB(O)c1cc2ccccc2c2ccccc12] | 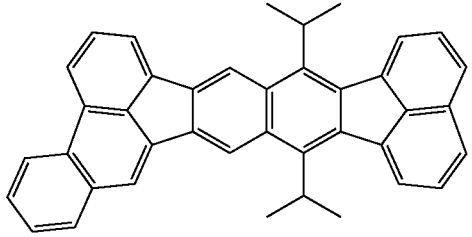 [SMILES: CC(C)c1c2cc3c(cc2c(C(C)C)c2c4cccc5cccc(c12)c54)c1cc2ccccc2c2cccc3c21] |
| Synthetic Example 14 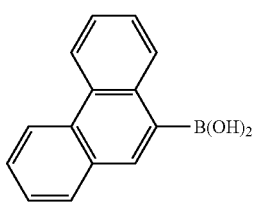 | 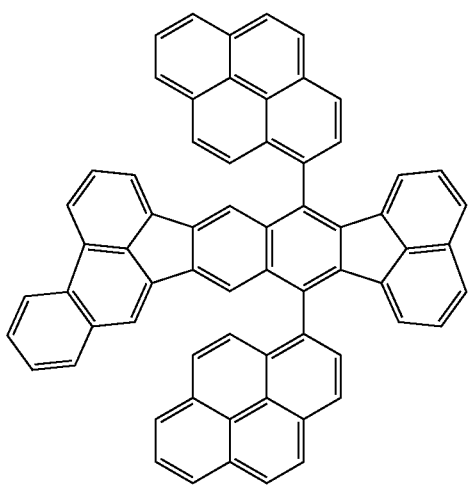 [SMILES: c1ccc2c(c1)cc1c3cc4c(-c5ccc6ccc7cccc8ccc5c6c78)c5c6cccc7cccc(c5c(-c5ccc8ccc9cccc%10ccc5c8c9%10)c4cc3c3cccc2c31)c76] |

TABLE 3-continued

Synthetic Example 15

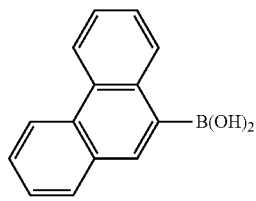 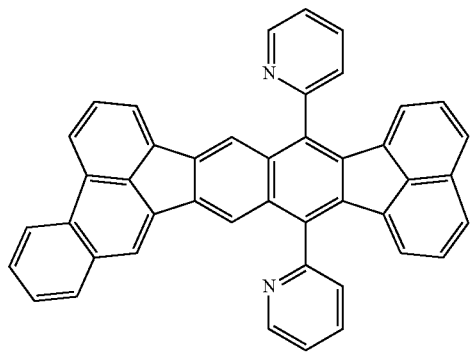 [SMILES: c1ccc(-c2c3cc4c(cc3c(-c3ccccn3)c3c5cccc6cccc(c23)c65)c2cc3ccccc3c3cccc4c32)nc1]

Synthetic Example 16

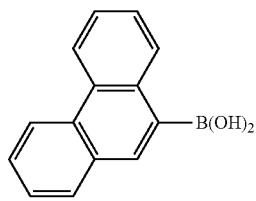 [SMILES: OB(O)c1cc2ccccc2c2ccccc12] 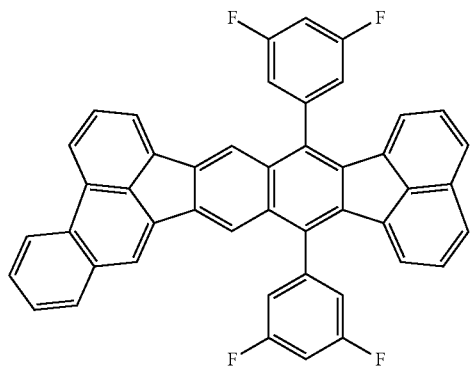 [SMILES: Fc1cc(F)cc(-c2c3cc4c(cc3c(-c3cc(F)cc(F)c3)c3c5cccc6cccc(c23)c65)c2cc3ccccc3c3cccc4c32)c1]

One embodiment of the organic light-emitting device will now be described.

An organic light-emitting device according to this embodiment includes a pair of electrodes, i.e., an anode and a cathode, and an organic compound layer interposed between the electrodes. This organic compound layer contains the organic compound represented by general formula (1) above. In the organic light-emitting device, the organic compound interposed between the electrodes functions as a light-emitting material and emits light.

In the case where a plurality of organic compound layers are provided and one of which is an emission layer, the emission layer may be entirely or partly composed of the organic compound of the present invention.

When the emission layer is partly composed of the organic compound of the present invention, the organic compound of the present invention may be the main component or a minor component of the emission layer.

The "main component" is, for example, a component with a large content in terms of weight or moles among all compounds constituting the emission layer. The "minor component" is the component with a small content.

The material that serves as the main component can also be called a "host material".

The material that serves as a minor component can be called "dopant (guest) material", "emitting assist material", or "charge injection material".

When the organic compound of this embodiment is used as a guest material, the guest material concentration relative to the host material can be 0.01 to 20 wt %, in particular, 0.5 to 10 wt %. The wavelength of the light emitted from the emission layer can be made longer than the wavelength of the solution by 5 nm to 20 nm by adjusting the concentration of the guest material in any one of these two ranges.

When the emission layer contains a host material and a guest material having a carrier transport property, the process that leads to emission includes following steps:
1. Transportation of electrons and holes inside the emission layer.
2. Generation of excitons of the host material.
3. Transfer of excitation energy among molecules of the host material.
4. Transfer of excitation energy from the host material to the guest material.

The energy transfer in the respective steps and the emission occur in competition with various deactivation processes.

Naturally, in order to enhance the emission efficiency of the organic light-emitting device, the emission quantum yield of the emission center material (e.g., guest material) itself must be high. However, one major challenge is how to efficiently transfer energy between the molecules of the host material and between the host material and the guest material. Although the exact cause of emission deterioration by electrical current is not yet clear, the inventors believe that the emission center material or the environmental changes brought to the emission center material by the nearby molecules may be attributable to the deterioration.

The inventors of the present invention have conducted various investigations and found that when a compound represented by general formula (1) of the present invention described above is used as the host or guest material or, in particular, as the guest material in the emission layer, the device outputs light highly efficiently at a high luminance and has considerably high durability.

The organic light-emitting device of this embodiment will now be described in detail.

The organic light-emitting device of this embodiment includes a pair of electrodes, i.e., an anode and a cathode, and an organic compound layer interposed between the electrodes. The organic compound layer contains at least one organic compound represented by general formula (1).

One or more compound layers other than the organic compound layer may be provided between the pair of electrodes.

In other words, two or more compound layers including the organic compound layer described above may be provided between the pair of electrodes. In such a case, the organic light-emitting device is called a multilayer organic light-emitting device.

First to fifth examples of multilayer organic light-emitting devices are described below.

A first example of a multilayer organic light-emitting device is a structure in which an anode, an emission layer, and a cathode are sequentially layered on a substrate. This type of organic light-emitting device is useful when a material having all of the hole transport property, the electron transport property, and the emission property by itself is used in the emission layer or when compounds having respective properties are mixed and used in the emission layer.

A second example a multilayer organic light-emitting device is a structure in which an anode, a hole transport layer, an electron transport layer, and a cathode are sequentially layered on a substrate. This type of organic light-emitting device is useful when a material having a hole transport property and a material having an electron transport property are respectively used in corresponding layers or when a material having both these properties is used in both layers in combination with a simple hole transport or electron transport substance that has no light-emitting property. In such a case, the emission layer is either the hole transport layer or the electron transport layer.

A third example of a multilayer organic light-emitting device is a structure in which an anode, a hole transport layer, an emission layer, an electron transport layer, and a cathode are sequentially layered on a substrate. In this structure, the carrier transport function and the light-emitting function are separated. Compounds respectively having a hole transport property, an electron transport property, and a light-emitting property may be adequately combined and used in the device. This significantly increases the flexibility of choices of materials. Moreover, since various different compounds with different emission wavelengths can be used, the variety of the emission hue can be widened. Carriers or excitons can be effectively confined in the center emission layer to enhance the emission efficiency.

A fourth example of a multilayer organic light-emitting device is a structure in which an anode, a hole injection layer, a hole transport layer, an emission layer, an electron transport layer, and a cathode are sequentially layered on a substrate. This structure improves the adhesiveness between the anode and the hole transport layer and improves the hole injectability, which is effective for decreasing the voltage.

A fifth example of a multilayer organic light-emitting device is a structure in which an anode, a hole transport layer, an emission layer, a hole/exciton-blocking layer, an electron transport layer, and a cathode are sequentially layered on a substrate. In this structure, a layer (hole/exciton-blocking layer) that prevents holes or excitons from reaching the cathode is interposed between the emission layer and the electron transport layer. Since a compound having a significantly high ionization potential is used in the hole/exciton-blocking layer, the emission efficiency can be effectively enhanced.

In the present invention, an emission region containing an organic compound represented by general formula (1) refers to a region of the emission layer described above.

The multilayer structures of the first to fifth examples are only the basic device structures and do not limit the structure of the organic light-emitting device that uses the organic compound of the present invention. For example, various other layer structures can be employed such as providing an insulating layer at the interface between an electrode and an organic layer, providing an adhesive layer or an interference layer, or designing the electron or hole transport layer to be made up of two layers with different ionization potentials.

The organic compound represented by general formula (1) used in the present invention may be used in any one of the first to fifth examples described above.

In the organic light-emitting device of this embodiment, the organic compound-containing layer contains at least one organic compound represented by general formula (1) of the present invention. In particular, the at least one organic compound represented by general formula (1) may be used as the guest material in the emission layer.

The organic compound of this embodiment may be used as the host material in the emission layer.

The organic compound of this embodiment may be used in any layers other than the emission layer such as a hole injection layer, a hole transport layer, a hole/exciton-blocking layer, an electron transport layer, and electron injection layer.

In addition to the organic compound of the present invention, existing low-molecular-weight and polymer hole transport compounds, light-emitting compounds, and electron transport compounds and the like may be used in combination if needed.

Examples of such compounds are as follows.

Hole injection/transport materials may have a high hole mobility so that holes can be easily injected from the anode and the injected holes can be transferred to the emission layer. Examples of the low-molecular-weight and polymer materials having hole injection/transport functions include, but are not limited to, triarylamine derivatives, phenylenediamine derivatives, stilbene derivatives, phthalocyanine derivatives, porphyrin derivatives, poly(vinyl carbazole), polythiophene, and other conductive polymers.

Examples of the host material include, but are not limited to, the compounds indicated in Table 4 and derivatives thereof; fused-ring compounds such as fluorene derivatives, naphthalene derivatives, anthracene derivatives, pyrene derivatives, carbazole derivatives, quinoxaline derivatives, and quinoline derivatives; organoaluminum derivatives such as tris(8-quinolinolato)aluminum; organic zinc complexes; and polymer derivatives such as triphenylamine derivatives, polyfluorene derivatives, and polyphenylene derivatives.

TABLE 4
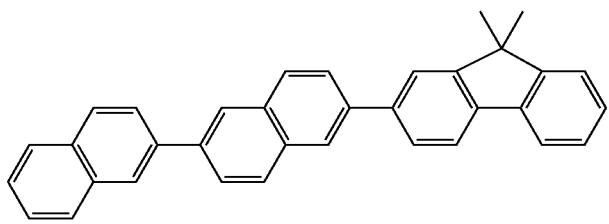 [SMILES: CC1(C)c2ccccc2-c2ccc(-c3ccc4cc(-c5ccc6ccccc6c5)ccc4c3)cc21]
H1
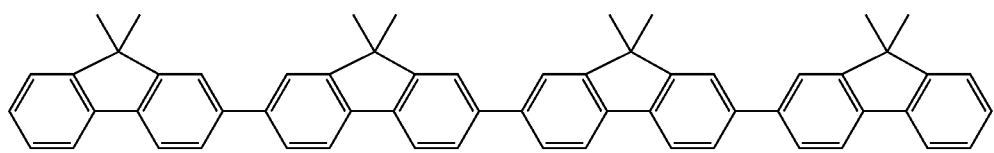 [SMILES: CC1(C)c2ccccc2-c2ccc(-c3ccc4c(c3)C(C)(C)c3cc(-c5ccc6c(c5)C(C)(C)c5cc(-c7ccc8c(c7)C(C)(C)c7ccccc7-8)ccc5-6)ccc3-4)cc21]
H2
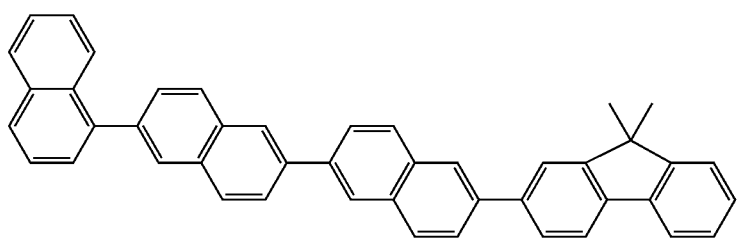 [SMILES: CC1(C)c2ccccc2-c2ccc(-c3ccc4cc(-c5ccc6cc(-c7cccc8ccccc78)ccc6c5)ccc4c3)cc21]
H3
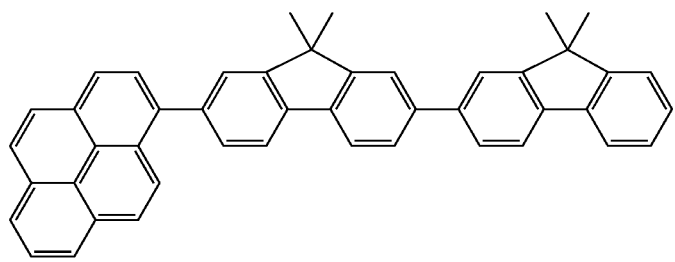 [SMILES: CC1(C)c2ccccc2-c2ccc(-c3ccc4c(c3)C(C)(C)c3cc(-c5ccc6ccc7cccc8ccc5c6c78)ccc3-4)cc21]
H4
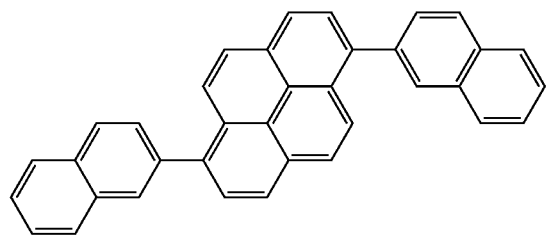 [SMILES: c1ccc2cc(-c3ccc4ccc5c(-c6ccc7ccccc7c6)ccc6ccc3c4c65)ccc2c1]
H5
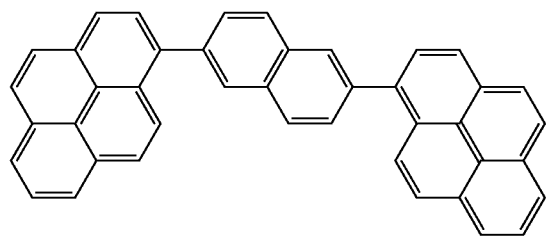 [SMILES: c1cc2ccc3ccc(-c4ccc5cc(-c6ccc7ccc8cccc9ccc6c7c89)ccc5c4)c4ccc(c1)c2c34]
H6

TABLE 4-continued
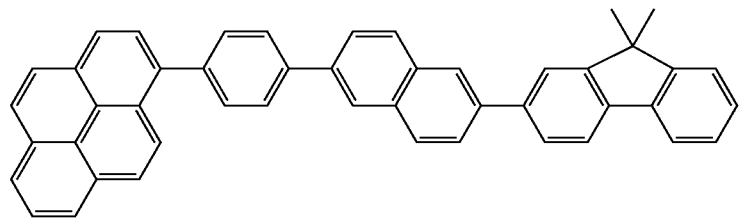 [SMILES: CC1(C)c2ccccc2-c2ccc(-c3ccc4cc(-c5ccc(-c6ccc7ccc8cccc9ccc6c7c89)cc5)ccc4c3)cc21]
H7
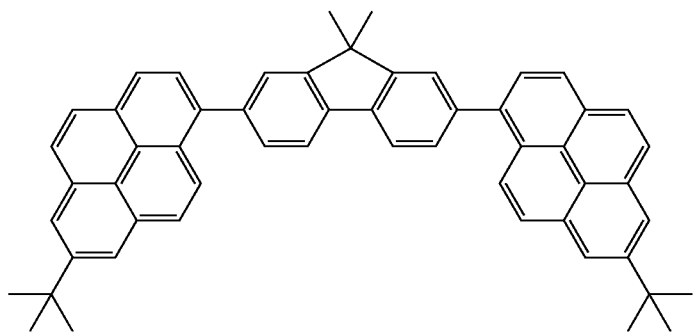 [SMILES: CC(C)(C)c1cc2ccc3ccc(-c4ccc5c(c4)C(C)(C)c4cc(-c6ccc7ccc8cc(C(C)(C)C)cc9ccc6c7c89)ccc4-5)c4ccc(c1)c2c34]
H8
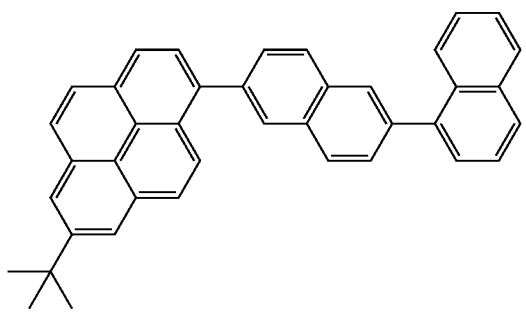 [SMILES: CC(C)(C)c1cc2ccc3ccc(-c4ccc5cc(-c6cccc7ccccc67)ccc5c4)c4ccc(c1)c2c34]
H9
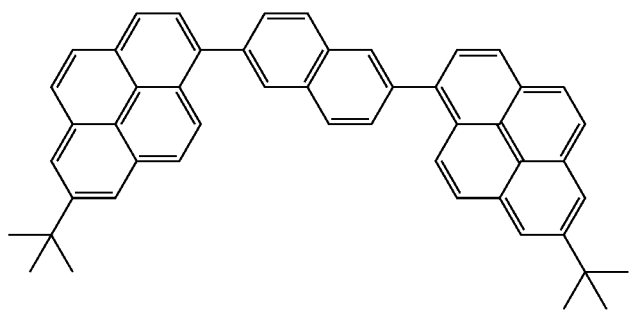 [SMILES: CC(C)(C)c1cc2ccc3ccc(-c4ccc5cc(-c6ccc7ccc8cc(C(C)(C)C)cc9ccc6c7c89)ccc5c4)c4ccc(c1)c2c34]
H10
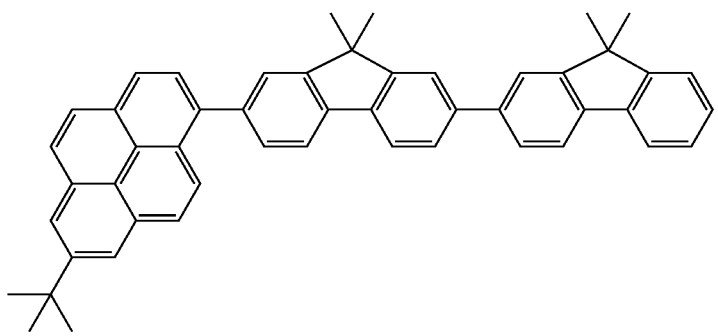 [SMILES: CC(C)(C)c1cc2ccc3ccc(-c4ccc5c(c4)C(C)(C)c4cc(-c6ccc7c(c6)C(C)(C)c6ccccc6-7)ccc4-5)c4ccc(c1)c2c34]
H11

TABLE 4-continued
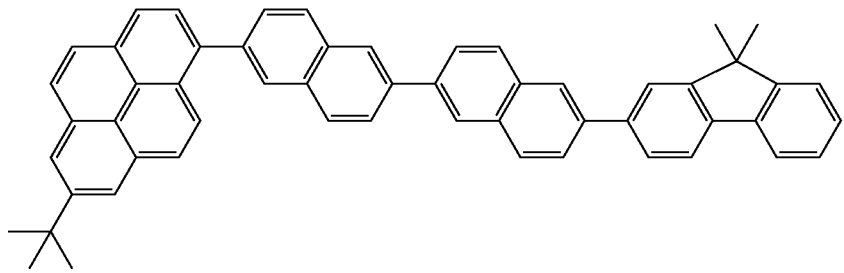 [SMILES: CC(C)(C)c1cc2ccc3ccc(-c4ccc5cc(-c6ccc7cc(-c8ccc9c(c8)C(C)(C)c8ccccc8-9)ccc7c6)ccc5c4)c4ccc(c1)c2c34]
H12
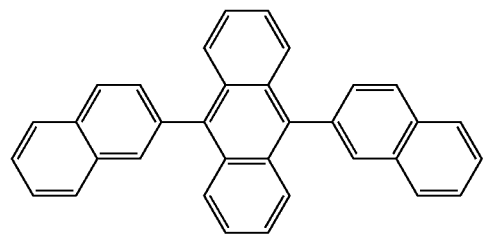 [SMILES: c1ccc2cc(-c3c4ccccc4c(-c4ccc5ccccc5c4)c4ccccc34)ccc2c1]
H13
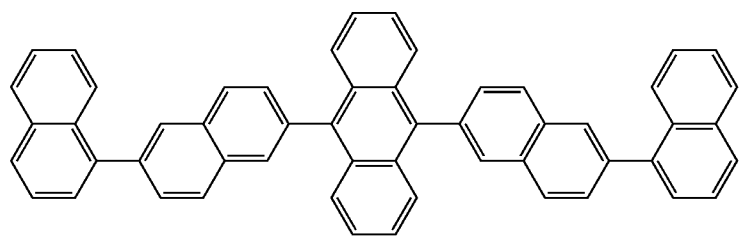 [SMILES: c1ccc2c(-c3ccc4cc(-c5c6ccccc6c(-c6ccc7cc(-c8cccc9ccccc89)ccc7c6)c6ccccc56)ccc4c3)cccc2c1]
H14
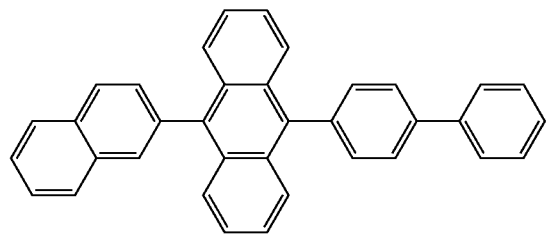 [SMILES: c1ccc(-c2ccc(-c3c4ccccc4c(-c4ccc5ccccc5c4)c4ccccc34)cc2)cc1]
H15
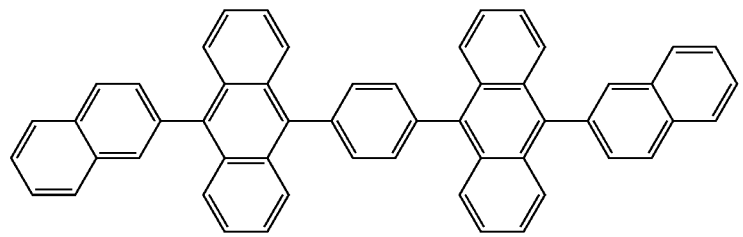 [SMILES: c1ccc2cc(-c3c4ccccc4c(-c4ccc(-c5c6ccccc6c(-c6ccc7ccccc7c6)c6ccccc56)cc4)c4ccccc34)ccc2c1]
H16
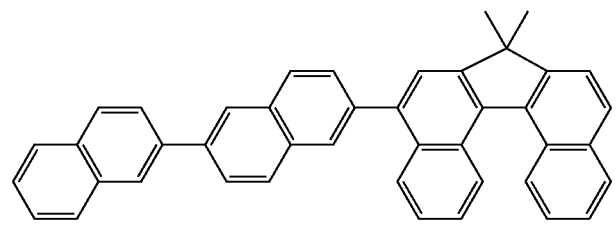 [SMILES: CC1(C)c2ccc3ccccc3c2-c2c1cc(-c1ccc3cc(-c4ccc5ccccc5c4)ccc3c1)c1ccccc21]
H17

TABLE 4-continued
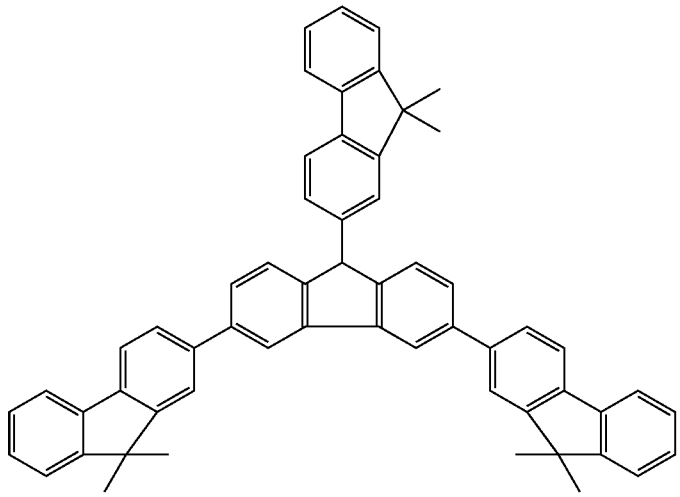 [SMILES: CC1(C)c2ccccc2-c2ccc(-c3ccc4c(c3)-c3cc(-c5ccc6c(c5)C(C)(C)c5ccccc5-6)ccc3C4c3ccc4c(c3)C(C)(C)c3ccccc3-4)cc21]
H18
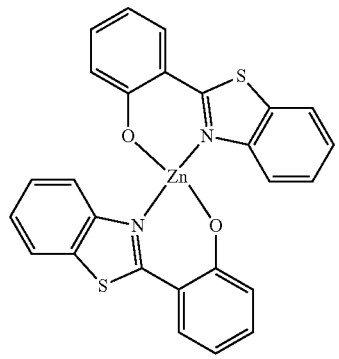
H19
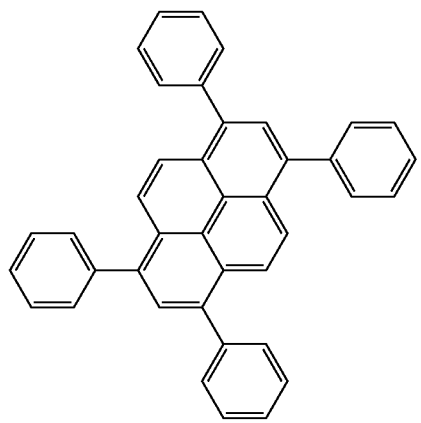 [SMILES: c1ccc(-c2cc(-c3ccccc3)c3ccc4c(-c5ccccc5)cc(-c5ccccc5)c5ccc2c3c54)cc1]
H20
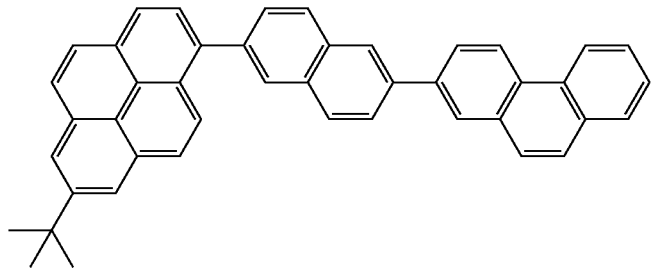 [SMILES: CC(C)(C)c1cc2ccc3ccc(-c4ccc5cc(-c6ccc7c(ccc8ccccc87)c6)ccc5c4)c4ccc(c1)c2c34]
H21

TABLE 4-continued
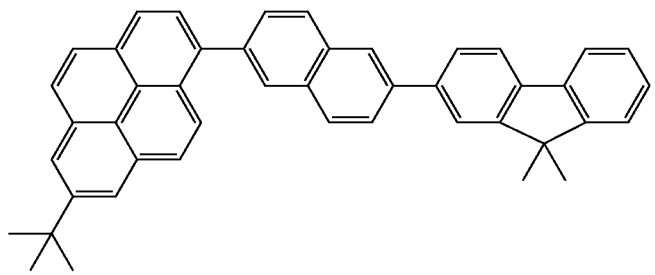 [SMILES: CC(C)(C)c1cc2ccc3ccc(-c4ccc5cc(-c6ccc7c(c6)C(C)(C)c6ccccc6-7)ccc5c4)c4ccc(c1)c2c34]
H22
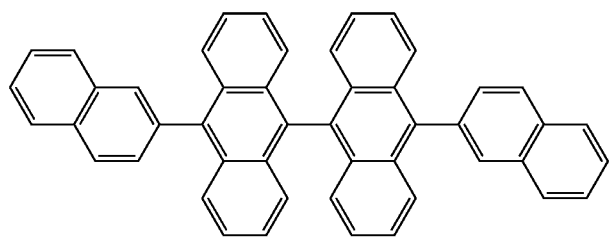 [SMILES: c1ccc2cc(-c3c4ccccc4c(-c4c5ccccc5c(-c5ccc6ccccc6c5)c5ccccc45)c4ccccc34)ccc2c1]
H23
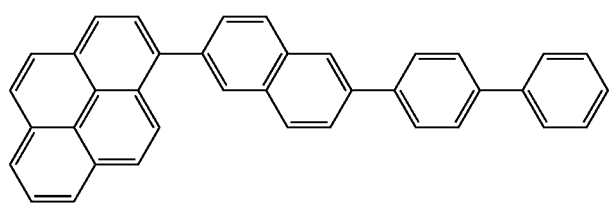 [SMILES: c1ccc(-c2ccc(-c3ccc4cc(-c5ccc6ccc7cccc8ccc5c6c78)ccc4c3)cc2)cc1]
H24
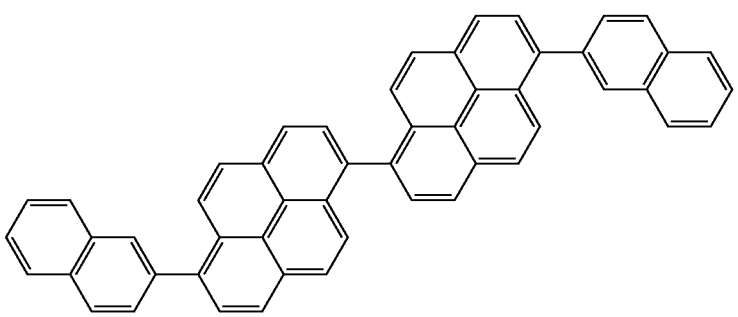 [SMILES: c1ccc2cc(-c3ccc4ccc5c(-c6ccc7ccc8c(-c9ccc%10ccccc%10c9)ccc9ccc6c7c98)ccc6ccc3c4c65)ccc2c1]
H25
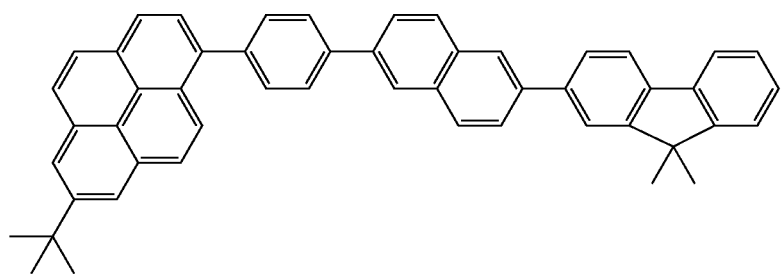 [SMILES: CC(C)(C)c1cc2ccc3ccc(-c4ccc(-c5ccc6cc(-c7ccc8c(c7)C(C)(C)c7ccccc7-8)ccc6c5)cc4)c4ccc(c1)c2c34]
H26

TABLE 4-continued

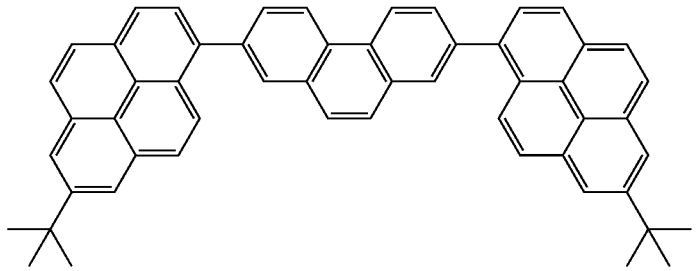 [SMILES: CC(C)(C)c1cc2ccc3ccc(-c4ccc5c(ccc6cc(-c7ccc8ccc9cc(C(C)(C)C)cc%10ccc7c8c9%10)ccc65)c4)c4ccc(c1)c2c34]

H27

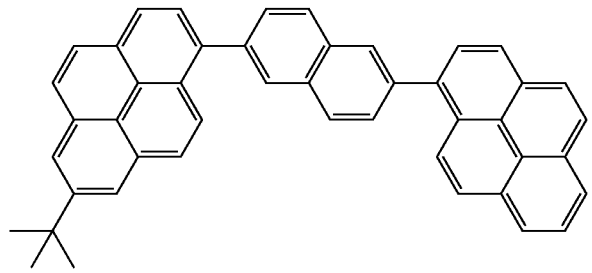 [SMILES: CC(C)(C)c1cc2ccc3ccc(-c4ccc5cc(-c6ccc7ccc8cccc9ccc6c7c89)ccc5c4)c4ccc(c1)c2c34]

H28

The hole injection/transport material can be adequately selected from those that allow easy injection of electrons from the cathode and that can transport the injected electrons to the emission layer. A material is selected by considering the balance with the hole mobility of the hole injection/transport material and the like. Examples of the materials having electron injection/transport properties include, but are not limited to, oxadiazole derivatives, oxazole derivatives, pyrazine derivatives, triazole derivatives, triazine derivatives, quinoline derivatives, quinoxaline derivatives, phenanthroline derivatives, and organoaluminum complexes.

The material for the anode may be a material that has a high work function. Examples thereof include single metals such as gold, platinum, silver, copper, nickel, palladium, cobalt, selenium, vanadium, and tungsten, and their alloys; and metal oxides such as tin oxide, zinc oxide, indium oxide, indium tin oxide (ITO), and zinc indium oxide. Electrically conductive polymers such as polyaniline, polypyrrole, polythiophene, and the like can also be used. These electrode substances may be used alone or in combination. The anode may have a single-layer structure or a multilayer structure.

In contrast, the material for the cathode may be a material that has a low work function. Examples of such a material include alkali metals such as lithium, alkaline earth metals such as calcium, and other single metals such as aluminum, titanium, manganese, silver, lead, and chromium. Alternatively, an alloy combining these single metals may also be used. Examples thereof include magnesium-silver, aluminum-lithium, and aluminum-magnesium. Metal oxides such as indium tin oxide (ITO) may also be used. These electrode substances may be used alone or in combination. The cathode may have a single-layer structure or a multilayer structure.

The substrate used in the organic light-emitting device of this embodiment is not particularly limited. For example, an opaque substrate such as a metal substrate or a ceramic substrate, or a transparent substrate such as a glass substrate, a quartz substrate, or a plastic sheet, may be used. A color filter film, a fluorescence color conversion filter film, a dielectric reflective film, or the like may be used to control the color of emission.

A protective layer or a sealing layer may be provided to the fabricated device in order to prevent the device from contacting oxygen, moisture, and the like. Examples of the protective layer include inorganic material films such as diamond thin films and metal oxide and metal nitride films; polymeric films of fluorocarbon resin, polyethylene, silicone resin, and polystyrene resin; and films of photocurable resin. The device may be covered with glass, a gas-impermeable film, a metal, or the like and packaged with an adequate sealing resin.

In the organic light-emitting device of this embodiment, a layer containing the organic compound of the present invention and layers containing other organic compounds are formed by the following methods. In general, thin films are formed by vacuum vapor deposition, ionization deposition, sputtering, plasma-enhanced deposition, and various existing coating techniques (e.g., spin-coating, dipping, casting, a Langmuir-Blodgett technique, and ink-jet) that involves dissolving the compounds in adequate solvents. When layers are formed by vacuum vapor deposition or a solution coating technique, crystallization and other unfavorable phenomena rarely occur and stability with time is excellent. When a coating technique is used to form films, an adequate binder resin may be used in combination.

Examples of the binder resin include, but are not limited to, polyvinyl carbazole resin, polycarbonate resin, polyester resin, ABS resin, acryl resin, polyimide resin, phenol resin, epoxy resin, silicone resin, and urea resin. These binder resins may be used alone as a homopolymer or in combination as a copolymer. If needed, existing additives such as a plasticizer, an antioxidant, and a UV absorber may be used in combination.

The organic light-emitting device of this embodiment can be applied to products that require energy saving and high luminance. Examples of the application include light sources of display apparatuses, lighting apparatuses, and printers, and backlights for liquid crystal display apparatuses.

When the organic light-emitting device is applied to a display apparatus, a high-visibility, light-weight, energy-saving flat panel display can be made. The display apparatus can be used as image-display apparatuses for personal computers, televisions, and advertising media. The display apparatus may be used in display units of image-capturing apparatuses such as digital still cameras and digital video cameras.

Alternatively, the display apparatus may be used in an operation display unit of an electrophotographic image-forming apparatus, e.g., a laser beam printer or a copier.

The organic light-emitting device may be used as a light source for exposing a latent image on a photosensitive member of an electrophotographic image-forming apparatus, e.g., a laser beam printer or a copier. A plurality of organic light-emitting devices that can be addressed independently may be arranged into an array (e.g., lines) and desired exposure may be conducted on a photosensitive drum to form a latent image. Since the organic light-emitting devices of this embodiment are used, the space which has been previously required for placing polygon mirrors, various optical lenses, and the like can be saved.

When the device is applied to lighting apparatuses and backlights, the effect of energy conservation can be expected. The organic light-emitting device of this embodiment can also be used as a flat light source.

Alternatively, a color filter film, a fluorescence color conversion filter film, a dielectric reflective film, and other associated components may be formed on the substrate supporting the organic light-emitting device of this embodiment to control the color of emission. A thin film transistor (TFT) may be formed on the substrate and be connected to the organic light-emitting device to control ON and OFF of the emission. A plurality of organic light-emitting devices may be arranged into a matrix, i.e., arranged in an in-plane direction, so that they can be used as a lighting apparatus.

Next, a display apparatus that uses the organic light-emitting device of this embodiment is described in detail. The display apparatus includes the organic light-emitting device of this embodiment and a unit configured to supply electrical signals to the organic light-emitting device of this embodiment. The display apparatus of this embodiment is described in detail below by taking an active matrix system as an example with reference to the drawings.

FIG. 1 is a schematic diagram illustrating an example of configuration of a display apparatus according to one embodiment. The display apparatus includes the organic light-emitting device of the embodiment and a unit configured to supply electrical signals to the organic light-emitting device of the embodiment.

Figure 2:
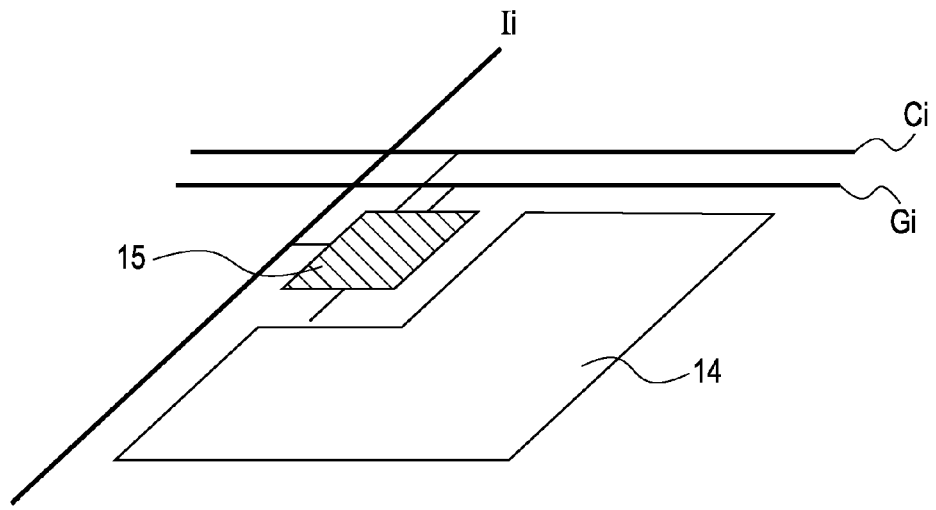
FIG. 2 is a schematic diagram showing a pixel circuit connected to a pixel and signal and electrical power supply lines connected to the pixel circuit.

FIG. 2 is a schematic diagram showing a pixel circuit connected to a pixel and signal and electrical current supply lines connected to the pixel circuit.

The unit configured to supply electrical signals to the organic light-emitting device of the embodiment includes a scan signal driver 11, a data signal driver 12, and an electrical current supply source 13 in FIG. 1 and a pixel circuit 15 in FIG. 2.

A display apparatus 1 shown in FIG. 1 includes the scan signal driver 11, the data signal driver 12, and the electrical current supply source 13 which are respectively connected to gate selection lines G, data signal lines I, and electrical current supply lines C. Pixel circuits 15 are arranged at intersections of the gate selection lines G and the data signal lines I, as shown in FIG. 2. One pixel 14 constituted by the organic light-emitting device of the embodiment is provided for each corresponding pixel circuit 15. In other words, the pixel 14 is an organic light-emitting device. In the drawing, the organic light-emitting device is illustrated as the emission point. Upper electrodes of the organic light-emitting devices may be formed as a common upper electrode for all of the organic light-emitting devices. Of course, the upper electrodes of the respective organic light-emitting devices may be formed separately.

The scan signal driver 11 sequentially selects gate selection lines G1, G2, G3, . . . and Gn, in synchronization with which image signals are applied to the pixel circuits 15 via one of data signal lines I1, I2, I3, . . . and In from the data signal driver 12.

Figure 3:
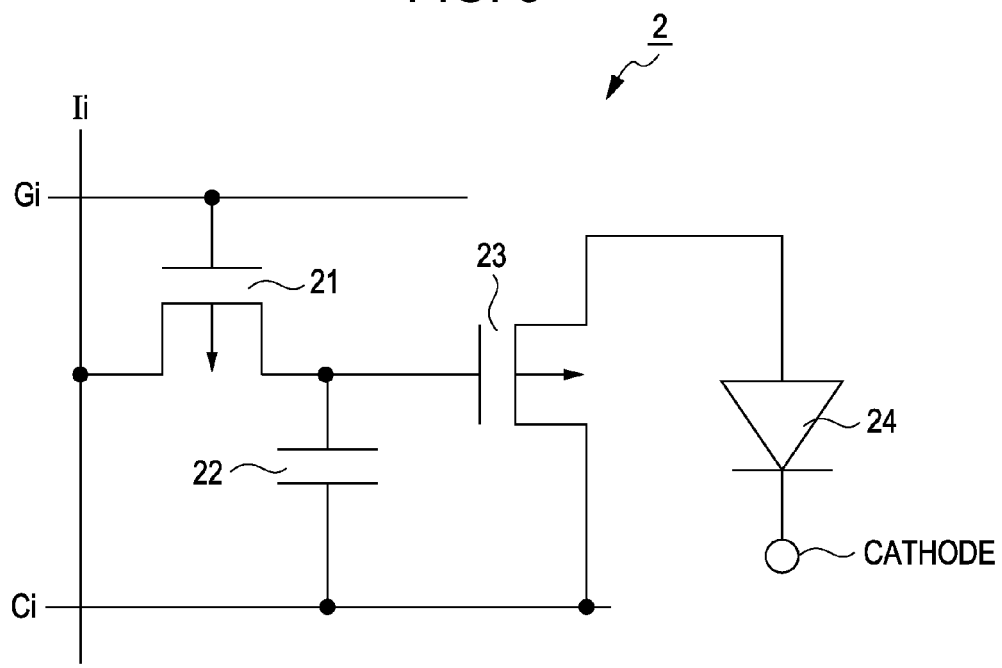
FIG. 3 is a circuit diagram showing the pixel circuit.

Next, operation of a pixel is described. FIG. 3 is a circuit diagram showing a circuit configuring one pixel in the display apparatus 1 shown in FIG. 1. In FIG. 3, a second thin film transistor (TFT) 23 controls the electrical current for causing an organic light-emitting device 24 to emit light. In a pixel circuit 2 in FIG. 3, when a selection signal is applied to a gate selection line Gi, the first TFT 21 is turned ON, an image signal Ii is supplied to a capacitor 22, and a gate voltage of the second TFT 23 is thereby determined. An electrical current is supplied to the organic light-emitting device 24 from an electrical current supply line Ci according to the gate voltage of the second TFT 23. Here, the gate potential of the second TFT 23 is retained in the capacitor 22 until the first TFT 21 is scanned and selected next. Accordingly, the electric current keeps flowing in the organic light-emitting device 24 until the next time scanning is performed. As a result, the organic light-emitting device 24 keeps emitting light during one frame period.

Although not shown in the drawings, the organic light-emitting device of this embodiment can be used in a voltage-write display apparatus in which the voltage between the electrodes of the organic light-emitting device 24 is controlled by a thin film transistor.

Figure 4:
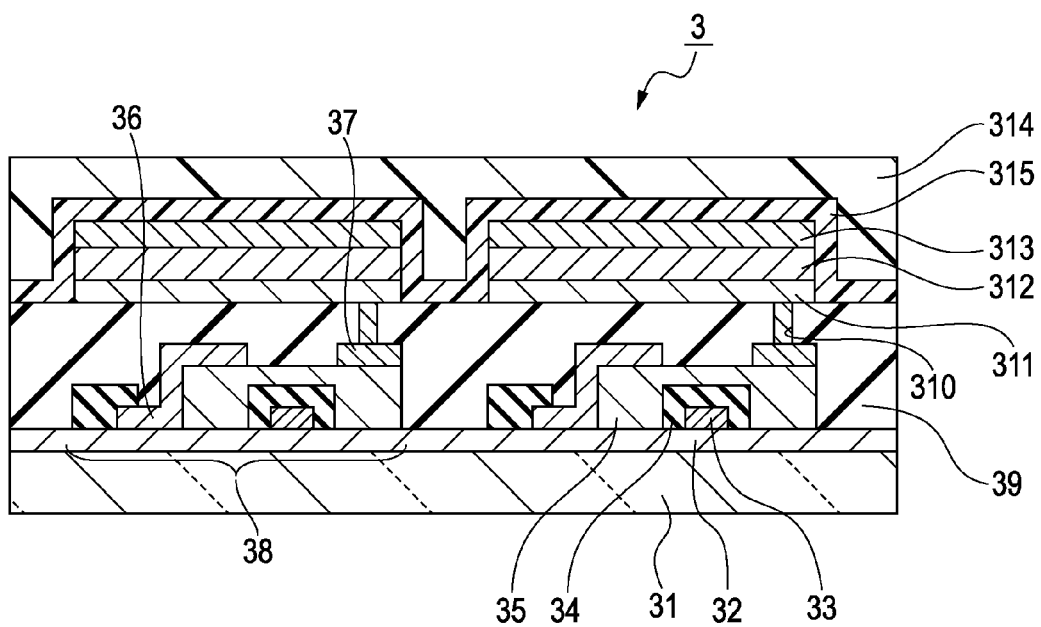
FIG. 4 is a schematic cross-sectional view of an organic light-emitting device and a thin film transistor under the organic light-emitting device.

FIG. 4 is a schematic view showing one example of a cross-sectional structure of a TFT substrate used in the display apparatus shown in FIG. 1. The detailed structure is described below by taking a method for making the TFT substrate as an example.

In making a display apparatus 3 shown in FIG. 4, first, a moisture-proof film 32 for protecting components (TFT or organic layer) formed thereon is formed on a substrate 31 composed of glass or the like by coating. Silicon oxide or a complex of silicon oxide and silicon nitride is used to form the moisture-proof film 32. Next, a metal film of Cr or the like is formed by sputtering and patterned into a particular circuit shape to form a gate electrode 33.

A film of silicon oxide or the like is formed by plasma-enhanced CVD or catalytic chemical vapor deposition (cat-CVD) and patterned to form a gate insulating film 34. A silicon film is formed by plasma-enhanced CVD or the like (annealing at a temperature of 290° C. or more if necessary) and patterned according to a circuit shape to form a semiconductor layer 35.

A drain electrode 36 and a source electrode 37 are formed on the semiconductor layer 35 to form a TFT element 38. As a result, a circuit as shown in FIG. 3 is formed. Next, an insulating film 39 is formed on the TFT element 38. A contact hole (through hole) 310 is formed to connect a metal anode 311 for the organic light-emitting device to the source electrode 37.

A multilayer or single-layer organic layer 312 and a cathode 313 are sequentially layered on the anode 311. As a result, the display apparatus 3 is obtained. A first protective layer 314 and a second protective layer 315 may be provided to prevent deterioration of the organic light-emitting device. In operation, the display apparatus using the organic light-emitting device of this embodiment can achieve stable display of high-quality images for a long period of time.

Note that the switching element of the display apparatus described above is not particularly limited, and the display apparatus can be applied even with a single crystal silicon substrate, a MIM device, an a-Si device, or the like.

An organic light-emitting display panel can be obtained by sequentially layering a single-layer or multilayer organic emission layer and a cathode layer on the ITO electrode. In operation, the display panel using the organic compound of the present invention can display high-quality images stably over a long time.

As for the direction in which the light is output from the device, either a bottom-emission structure (light is output from the substrate side) or a top-emission structure (light is output from the side opposite the substrate) is applicable.

The present invention will now be described in further detail by using non-limiting examples.

EXAMPLES

Example 1

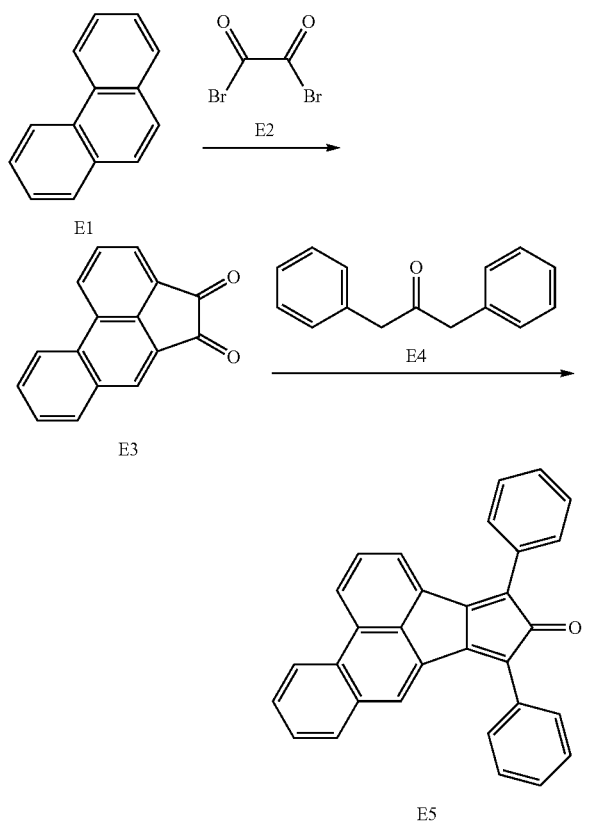

[Synthesis of Example Compound A2]

Into 500 ml of carbon disulfide, 17.8 g (100 mmol) phenanthrene (E1), 21.5 g (100 mmol) E2, and 26.6 g (100 mol) aluminum bromide were mixed at −40° C., and the resulting mixture was stirred for 3 hours. After the temperature of the mixture had returned to room temperature, stirring was conducted for 1 hour. The mixture was discharged into water and precipitates were filtered, washed with ethanol, and dried. As a result, 20 g (yield: 85%) of an ocher solid E3 was obtained. To 200 ml of ethanol, 11.6 g (50 mmol) E3 obtained as such and 10.5 g (50 mmol) of E4 were added, and the resulting mixture was heated to 60° C. To the resulting mixture, 20 ml of a 5M aqueous sodium hydroxide solution was added dropwise. Upon completion of the dropwise addition, the mixture was heated to 80° C., stirred for 2 hours, and cooled. Precipitates were filtered, washed with water and ethanol, and vacuum-dried under heating at 80° C. As a result, 18.2 g (yield: 95%) of a dark green solid E5 was obtained.

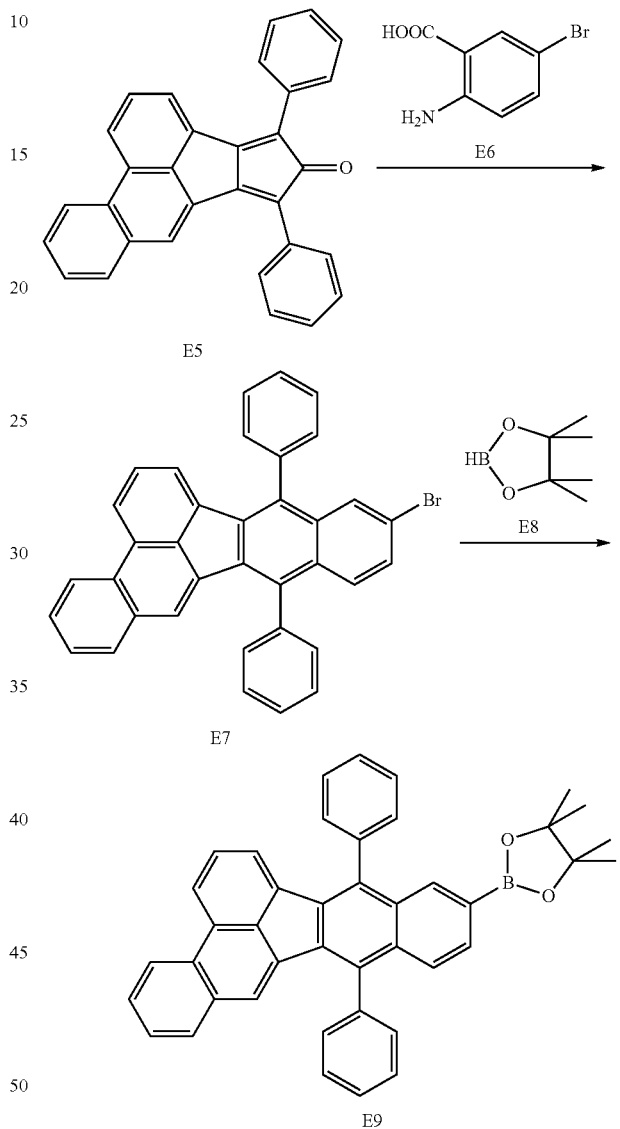

Next, into 100 ml of toluene, 4.1 g (10 mmol) E5 and 2.7 g (11 mmol) E6 were added, and the resulting mixture was heated to 80° C. Then 1.3 g (11 mmol) of isoamyl nitrite was slowly added dropwise, and the resulting mixture was stirred for 3 hours at 110° C. After cooling, the mixture was washed twice with 100 ml of water each time. The organic layer was washed with saturated saline and dried with magnesium sulfate. The resulting solution was filtered and the filtrate was concentrated to obtain a brown liquid. After the brown liquid had been purified by column chromatography (toluene/heptane=1:1), recrystallization was conducted with chloroform/methanol to obtain 4.37 g (yield 82%) of E7 in form of yellow crystals. Into 50 ml of toluene, 4.3 g (8 mmol) E7, 870 m g (1.6 mmol) [1,3-(diphenylphosphinopropane)]nickel(II)

chloride, 2.0 g (16 mmol) E8 were added, and the resulting mixture was stirred. To the resulting mixture, 1.6 g (16 mmol) triethylamine was added. The mixture was heated to 90° C. and then stirred for 6 hours. After cooling and filtration, the filtrate was washed twice with 100 ml of water each time. The organic layer was washed with saturated saline and dried with magnesium sulfate. The resulting solution was filtered and the filtrate was concentrated to obtain a brown liquid. After the brown liquid had been purified by column chromatography (toluene), recrystallization was conducted with toluene/methanol to obtain 3.0 g (yield: 64%) of E9 in form of pale yellow crystals.

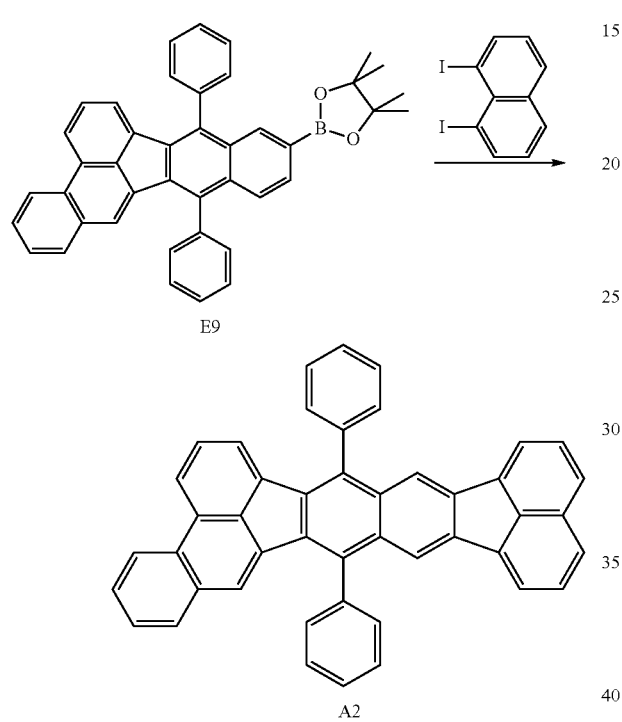

Next, 580 mg (1.0 mmol) E9, 456 mg (1.2 mmol) 1,8-diiodonaphthalene, 91 mg (0.1 mmol) tris(dibenzylideneacetone)dipalladium(0), 100 mg (0.3 mmol) tricyclohexylphosphine, 0.75 ml diazabicycloundecene, and 5 ml dimethylformamide were heated to reflux, and the resulting mixture was stirred for 12 hours. After cooling, 20 ml chloroform was added, and the filtrate was washed twice with 100 ml of water each time. The organic layer was washed with saturated saline and dried with magnesium sulfate. The resulting solution was filtered and the filtrate was concentrated to obtain a yellow liquid. After the yellow liquid had been purified by column chromatography (toluene/heptane=1:8), recrystallization was conducted with chloroform/methanol to obtain 347 mg (yield 60%) of Example Compound A2 in form of yellow crystals.

The structure of the compound was confirmed by NMR spectroscopy.

$^1$H NMR (CDCl$_3$, 500 MHz) σ (ppm): 8.57 (d, 1H, J=6.4 Hz), 8.37 (d, 1H, J=6.4 Hz), 8.14 (d, 2H, J=11.2 Hz), 7.89-7.45 (m, 20H), 6.82 (s, 1H), 6.66 (d, 1H, J=6.0 Hz).

The emission spectrum of a 1×10$^{-5}$ mol/l toluene solution of Example Compound A2 was measured with F-4500 produced by Hitachi Ltd., and photoluminescence was measured at a 350 nm excitation wavelength. The spectrum had the maximum intensity at 457 nm.

Comparative Examples 1 and 2

Compounds F1 and F2 were synthesized as comparative examples to compare the quantum efficiency on the basis of measurement of the photoluminescence and absorption spectrum. The absorption spectrum was measured with UV-570 produced by JASCO Corporation. The quantum yield was calculated as a relative strength with respect to 1.0 of Example Compound A2.

TABLE 5

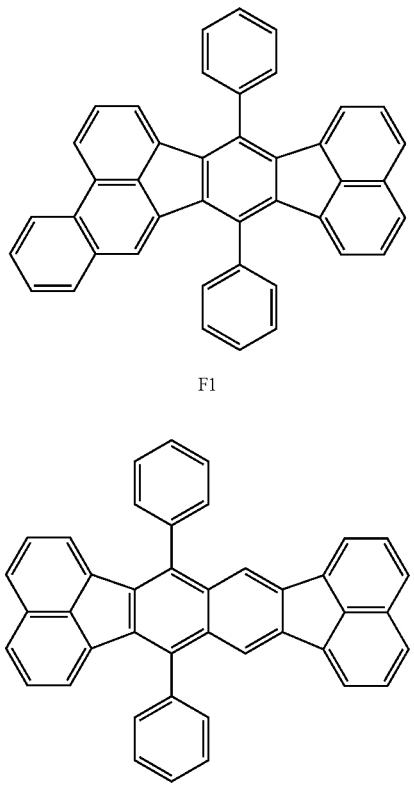

| | Example compound A2 | Comparative Compound F1 | Comparative Compound F2 |
|---|---|---|---|
| Emission wavelength (nm) | 457 | 490 | 455 |
| Quantum yield | 1.0 | 0.2 | 0.9 |

It was found that the organic compounds of the present invention achieve high quantum yields in the blue emission range.

Example 2

Synthesis of Example Compound A6

The same reactions and purification were conducted as in Example 1 except that the organic compound was changed from E4 to E10.

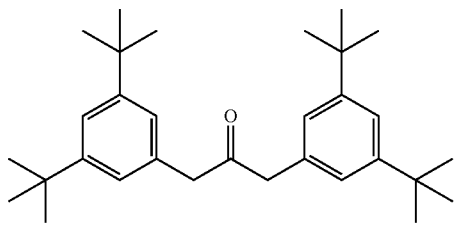

E10

The emission spectrum of a 1×10⁻⁵ mol/l toluene solution of Example Compound A6 was measured with F-4500 produced by Hitachi Ltd., and photoluminescence was measured at a 350 nm excitation wavelength. The spectrum had the maximum intensity at 459 nm.

Examples 3 to 19

In Examples 3 to 19, multilayer organic light-emitting devices of the fifth example (anode/hole injection layer/hole transport layer/emission layer/hole- and exciton-blocking layer/electron transport layer/cathode) were prepared. In each example, an ITO film 100 nm in thickness was formed on a glass substrate by patterning. The following organic and electrode layers were then continuously formed on the ITO substrate by resistance heating vapor deposition in a vacuum chamber at $10^{-5}$ Pa so that the area of the electrodes facing each other was 3 mm².

Hole transport layer (30 nm): G-1
Emission layer (30 nm), Host: G-2, Guest: Example Compound (weight ratio: 5%)
Hole/exciton-blocking layer (10 nm): G-3
Electron transport layer (30 nm): G-4
Metal electrode layer 1 (1 nm): LiF
Metal electrode layer 2 (100 nm): Al

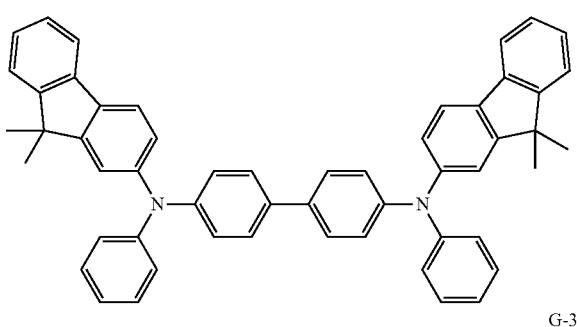

G-1

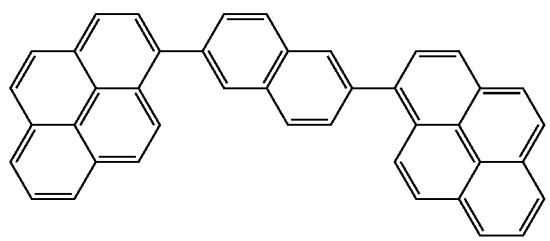

G-3

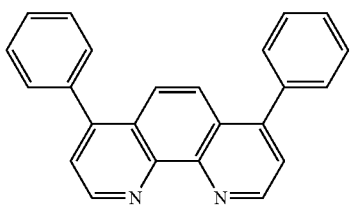

G-4

The current-voltage characteristic of each EL device was measured with a pA meter 4140B produced by Hewlett-Packard Corporation and the luminance of emission was measured with BM7 produced by Topcon Corporation.

The emission efficiency and the voltage observed in Examples 3 to 19 are shown Table 6 below.

TABLE 6

| | Guest | G-2 | Emission efficiency (cd/A) | Voltage (V) |
|---|---|---|---|---|
| EXAMPLE 3 | A1 | H8 | 4.9 | 4.7 |
| EXAMPLE 4 | A2 | H10 | 4.1 | 4.5 |
| EXAMPLE 5 | A2 | H28 | 4.9 | 4.8 |
| EXAMPLE 6 | A3 | H5 | 4.5 | 4.4 |
| EXAMPLE 7 | A3 | H22 | 5.1 | 4.5 |
| EXAMPLE 8 | A6 | H21 | 5.8 | 4.2 |
| EXAMPLE 9 | A7 | H17 | 4.3 | 4.3 |
| EXAMPLE 10 | A17 | H2 | 5.1 | 4.6 |
| EXAMPLE 11 | A23 | H8 | 4.6 | 4.4 |
| EXAMPLE 12 | A24 | H23 | 4.4 | 4.4 |
| EXAMPLE 13 | A28 | H11 | 4.9 | 4.7 |
| EXAMPLE 14 | A36 | H27 | 5.0 | 4.2 |
| EXAMPLE 15 | A37 | H8 | 4.1 | 4.0 |
| EXAMPLE 16 | A52 | H17 | 3.9 | 4.6 |
| EXAMPLE 17 | A67 | H4 | 4.0 | 4.5 |
| EXAMPLE 18 | B3 | H6 | 3.6 | 5.0 |
| EXAMPLE 19 | B16 | H18 | 3.9 | 5.2 |

<Results and Studies>

The organic compounds of the present invention are novel compounds that achieve high quantum yields and emission suitable for blue emission. When the organic compounds are used in organic light-emitting devices, the organic light-emitting devices can exhibit good emission characteristics.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2008-324469, filed Dec. 19, 2008, which is hereby incorporated by reference herein in its entirety.

The invention claimed is:
1. An organic compound represented by general formula (1):

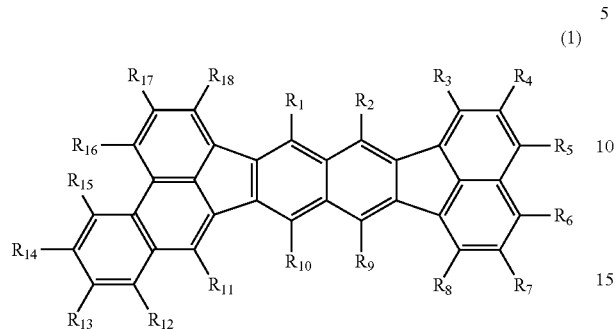

where $R_1$ to $R_{18}$ are each independently selected from a hydrogen atom, a halogen atom, a substituted or unsubstituted alkyl group, a substituted or unsubstituted alkoxy group, a substituted or unsubstituted amino group, a substituted or unsubstituted aryl group, and a substituted or unsubstituted heterocyclic group.

* * * * *